United States Patent
Takei et al.

(10) Patent No.: US 12,220,236 B2
(45) Date of Patent: Feb. 11, 2025

(54) EVALUATION DEVICE, EVALUATION METHOD, AND NON-TRANSITORY COMPUTER-READABLE RECORDING MEDIUM

(71) Applicant: JVCKENWOOD Corporation, Yokohama (JP)

(72) Inventors: Hiroyuki Takei, Yokohama (JP); Makoto Kito, Yokohama (JP)

(73) Assignee: JVCKENWOOD Corporation, Yokohama (JP)

( * ) Notice: Subject to any disclaimer, the term of this patent is extended or adjusted under 35 U.S.C. 154(b) by 830 days.

(21) Appl. No.: 17/383,482

(22) Filed: Jul. 23, 2021

(65) Prior Publication Data

US 2021/0345924 A1 Nov. 11, 2021

Related U.S. Application Data

(63) Continuation of application No. PCT/JP2019/044552, filed on Nov. 13, 2019.

(30) Foreign Application Priority Data

Feb. 12, 2019 (JP) ................. 2019-022521

(51) Int. Cl.
*A61B 5/16* (2006.01)
*A61B 5/00* (2006.01)

(52) U.S. Cl.
CPC ............ *A61B 5/163* (2017.08); *A61B 5/168* (2013.01); *A61B 5/742* (2013.01)

(58) Field of Classification Search
None
See application file for complete search history.

(56) References Cited

U.S. PATENT DOCUMENTS

2020/0329961 A1* 10/2020 Oz .................. A61H 5/005

FOREIGN PATENT DOCUMENTS

JP 2011-083403 4/2011

OTHER PUBLICATIONS

International Search Report and Written Opinion for International Application No. PCT/JP2019/044552 mailed on Jan. 28, 2020, 7 pages.

* cited by examiner

*Primary Examiner* — Michael R Bloch
(74) *Attorney, Agent, or Firm* — Amin, Turocy & Watson, LLP

(57) ABSTRACT

An evaluation device includes a display unit; a gaze point detection unit detecting a position of a gaze point of a subject; a display control unit causing the display unit to display a video for task of causing the subject to gaze at a final arrival point of a moving object; a region setting unit setting a movement route region corresponding to a movement route of the moving object according to a movement rule and a final arrival point region corresponding to the final arrival point; a determination unit determining, based on the position of the gaze point, whether the gaze point exists in the movement route region and the final arrival point region in a display period; a calculation unit calculating gaze point data in the display period based on a determination result; and an evaluation unit obtaining evaluation data of the subject based on the gaze point data.

5 Claims, 15 Drawing Sheets

EVALUATION DEVICE, EVALUATION METHOD, AND NON-TRANSITORY COMPUTER-READABLE RECORDING MEDIUM

CROSS-REFERENCE TO RELATED APPLICATION

This application is a Continuation of PCT International Application No. PCT/JP2019/044552 filed on Nov. 13, 2019 which claims the benefit of priority from Japanese Patent Application No. 2019-022521 filed on Feb. 12, 2019, the entire contents of both of which are incorporated herein by reference.

BACKGROUND OF THE INVENTION

1. Field of the Invention

The present invention relates to an evaluation device, an evaluation method, and a non-transitory computer-readable recording medium.

2. Description of the Related Art

In recent years, it is said that cognitive dysfunction such as dementia and brain dysfunction tend to increase. Further, it is required to detect such cognitive dysfunction and brain dysfunction at an early stage and quantitatively evaluate the severity of symptoms. For example, there has been proposed a device that displays a plurality of types of objects and checks an answer obtained by making a subject count the number of the objects (see, for example, JP 2011-083403 A).

In the above method, an answer is merely selected. It is difficult to verify whether the selected answer is an inevitably selected answer or an accidentally selected answer. Thus, there is room for improvement in the accuracy of the evaluation of a subject.

SUMMARY OF THE INVENTION

An evaluation device according to an aspect of the present disclosure includes a display unit, a gaze point detection unit, a display control unit, a region setting unit, a determination unit, a calculation unit, and an evaluation unit. The gaze point detection unit detects a position of a gaze point of a subject observing the display unit. The display control unit causes the display unit to display a video for a task of causing the subject to gaze at a final arrival point of a moving object. The region setting unit sets a movement route region corresponding to a movement route along which the moving object moves according to a movement rule and a final arrival point region corresponding to the final arrival point. The determination unit determines, on a basis of the position of the gaze point, whether the gaze point exists in the movement route region and the final arrival point region in a display period in which the video for the task is displayed. The calculation unit calculates gaze point data in the display period on a basis of a determination result of the determination unit. The evaluation unit obtains evaluation data of the subject on a basis of the gaze point data.

An evaluation method according to an aspect of the present disclosure includes displaying an image on a display unit; detecting a position of a gaze point of a subject observing the display unit; causing the display unit to display a video for a task of causing the subject to gaze at a final arrival point of a moving object; setting a movement route region corresponding to a movement route along which the moving object moves according to a movement rule and a final arrival point region corresponding to the final arrival point; determining, on a basis of the position of the gaze point, whether the gaze point exists in the movement route region and the final arrival point region in a display period in which the video for the task is displayed; calculating gaze point data in the display period on a basis of a determination result of the determining; and obtaining evaluation data of the subject on a basis of the gaze point data.

A non-transitory computer-readable recording medium according to an aspect of the present disclosure contains an evaluation program. The evaluation program causes a computer to execute displaying an image on a display unit; detecting a position of a gaze point of a subject observing the display unit; causing the display unit to display a video for a task of causing the subject to gaze at a final arrival point of a moving object; setting a movement route region corresponding to a movement route along which the moving object moves according to a movement rule and a final arrival point region corresponding to the final arrival point; determining, on a basis of the position of the gaze point, whether the gaze point exists in the movement route region and the final arrival point region in a display period in which the video for the task is displayed; calculating gaze point data in the display period on a basis of a determination result of the determining; and obtaining evaluation data of the subject on a basis of the gaze point data.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Hereinafter, embodiments of an evaluation device, an evaluation method, and an evaluation program according to the present disclosure will be described with reference to the drawings. Incidentally, the present invention is not limited by the embodiments. Further, constituent elements in the following embodiments include those that can be easily replaced by those skilled in the art or those that are substantially the same.

In the following description, a three-dimensional global coordinate system is set and positional relationships among respective portions will be described. A direction parallel to a first axis of a predetermined plane is defined as an X-axis direction, a direction parallel to a second axis of a predetermined plane orthogonal to the first axis is defined as a Y-axis direction, and a direction parallel to a third axis orthogonal to each of the first axis and the second axis is defined as a Z-axis direction. The predetermined plane includes an XY plane.

First Embodiment

Evaluation Device

Figure 1:
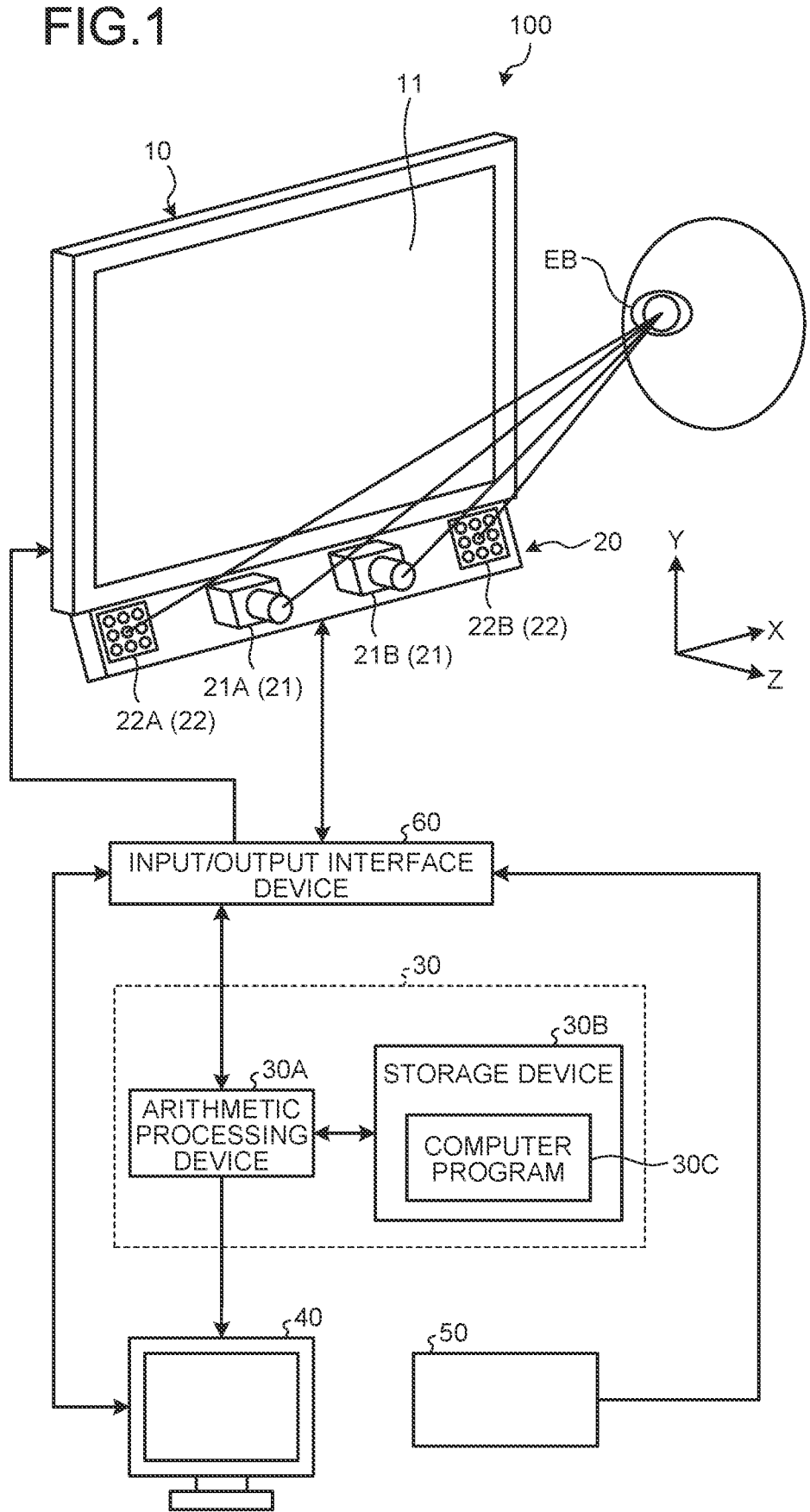
FIG. 1 is a diagram schematically illustrating an example of an evaluation device according to a first embodiment.

FIG. 1 is a diagram schematically illustrating an example of an evaluation device 100 according to this embodiment. The evaluation device 100 according to this embodiment detects the line-of-sight of a subject and evaluates cognitive dysfunction and brain dysfunction by using a detection result. The evaluation device 100 can detect the line-of-sight of the subject by various methods such as a method of detecting the line-of-sight on the basis of the position of the pupil of the subject and the position of a corneal reflection image or a method of detecting the line-of-sight on the basis of the position of the inner corner of the eye and the position of the iris of the subject.

As illustrated in FIG. 1, the evaluation device 100 includes a display device 10, an image acquisition device 20, a computer system 30, an output device 40, an input device 50, and an input/output interface device 60. The display device 10, the image acquisition device 20, the computer system 30, the output device 40, and the input device 50 perform data communication via the input/output interface device 60. Each of the display device 10 and the image acquisition device 20 includes a drive circuit (not illustrated).

The display device 10 includes a flat panel display such as a liquid crystal display (LCD) or an organic electroluminescence display (OLED). In this embodiment, the display device 10 includes a display unit 11. The display unit 11 displays information such as an image. The display unit 11 is substantially parallel to the XY plane. The X-axis direction is a horizontal direction of the display unit 11, the Y-axis direction is a vertical direction of the display unit 11, and the Z-axis direction is a depth direction orthogonal to the display unit 11. The display device 10 may be a head-mounted display device. In the case of a head-mounted display, a configuration such as the image acquisition device 20 is arranged in a head-mounted module.

The image acquisition device 20 acquires the image data of right and left eyeballs EB of the subject, and transmits the acquired image data to the computer system 30. The image acquisition device 20 includes an imaging device 21. The imaging device 21 acquires image data by photographing the right and left eyeballs EB of the subject. The imaging device 21 includes various cameras according to a method of detecting the line-of-sight of the subject. For example, in the case of a method of detecting the line-of-sight on the basis of the position of the pupil of the subject and the position of the corneal reflection image, the imaging device 21 includes an infrared camera, and includes, for example, an optical system capable of transmitting near-infrared light having a wavelength of 850 nm and an imaging element capable of receiving the near-infrared light. Furthermore, for example, in the case of a method of detecting the line-of-sight on the basis of the position of the inner corner of the eye and the position of the iris of the subject, the imaging device 21 includes a visible light camera. The imaging device 21 outputs a frame synchronization signal. The cycle of the frame synchronization signal can be, for example, 20 (msec), but is not limited thereto. The imaging device 21 can be configured as, for example, a stereo camera including a first camera 21A and a second camera 21B, but is not limited thereto.

For example, in the case of a method of detecting the line-of-sight on the basis of the position of the pupil of the subject and the position of the corneal reflection image, the image acquisition device 20 includes an illumination device 22 that illuminates the eyeball EB of the subject. The illumination device 22 includes a light emitting diode (LED) light source, and can emit, for example, near-infrared light having a wavelength of 850 nm. For example, in the case of a method of detecting a line-of-sight vector on the basis of the position of the inner corner of the eye and the position of the iris of the subject, the illumination device 22 may not be provided. The illumination device 22 emits detection light in synchronization with a frame synchronization signal of the imaging device 21. The illumination device 22 can be configured to include, for example, a first light source 22A and a second light source 22B, but is not limited thereto.

The computer system 30 comprehensively controls the operation of the evaluation device 100. The computer system 30 includes an arithmetic processing device 30A and a storage device 30B. The arithmetic processing device 30A includes a microprocessor such as a central processing unit (CPU). The storage device 30B includes a memory or a storage such as a read only memory (ROM) and a random access memory (RAM). The arithmetic processing device 30A performs arithmetic processing according to a computer program 30C stored in the storage device 30B.

The output device 40 includes a display device such as a flat panel display. The output device 40 may include a printing device. The input device 50 generates input data by being operated. The input device 50 includes a keyboard or a mouse for a computer system. The input device 50 may include a touch sensor provided on a display unit of the output device 40 that is a display device.

In the evaluation device 100 according to this embodiment, the display device 10 and the computer system 30 are separate devices. Alternatively, the display device 10 and the computer system 30 may be integrated. For example, the evaluation device 100 may include a tablet personal computer. In this case, a display device, an image acquisition device, a computer system, an input device, an output device, and the like may be mounted on the tablet personal computer.

Figure 2:
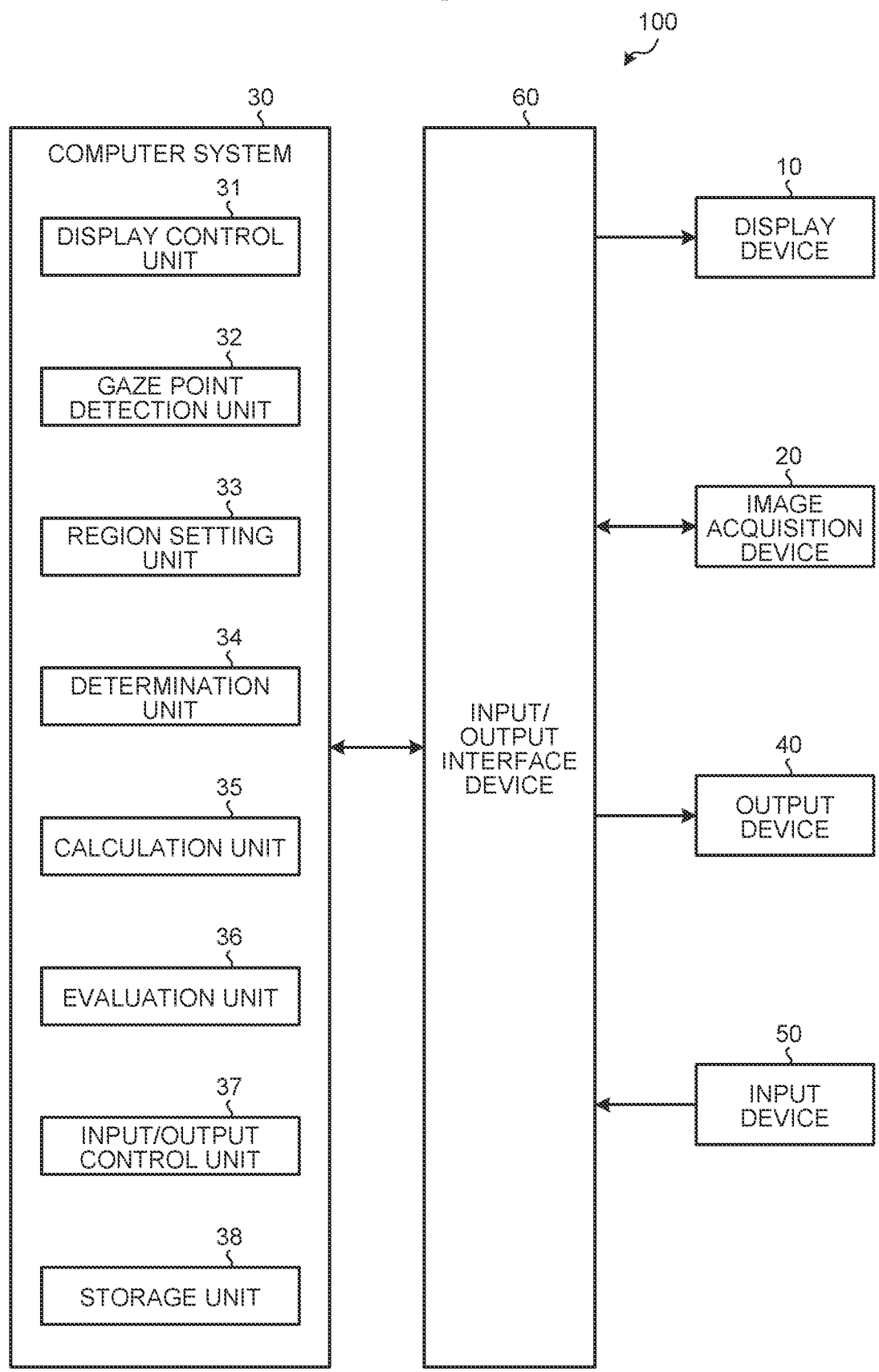
FIG. 2 is a functional block diagram illustrating an example of the evaluation device according to the first embodiment.

FIG. 2 is a functional block diagram illustrating an example of the evaluation device 100. As illustrated in FIG. 2, the computer system 30 includes a display control unit 31, a gaze point detection unit 32, a region setting unit 33, a determination unit 34, a calculation unit 35, an evaluation unit 36, an input/output control unit 37, and a storage unit 38. The functions of the computer system 30 are exerted by the arithmetic processing device 30A and the storage device 30B (see FIG. 1). Some functions of the computer system 30 may be provided outside the evaluation device 100.

The display control unit 31 causes the display unit 11 to display a task of causing the subject to gaze at the final arrival point of a moving object. In other words, the display control unit 31 causes the display unit 11 of the display device 10 to display the evaluation video to be visually recognized by the subject. The evaluation video is a video for a task of causing the subject to gaze at the movement route of the movement according to a movement rule and the final arrival point. The evaluation video includes a movement route and a final arrival point. The movement route is a route from a designated start point to the final arrival point. The movement route is uniquely determined according to the movement rule. The evaluation video may include a moving object moving along the movement route to the final arrival point on the movement route. The evaluation video may further include a restraint object which restrains the movement route and a comparison arrival point different from the final arrival point. The movement rule may be, for example, a natural law or an artificial law such as a maze or a ladder lot. The evaluation video includes a teaching video, a question video, and an answer video. The evaluation video is not limited to the video including all of the teaching video, the question video, and the answer video, and may be, for example, only the question video. The display form of the evaluation video is not limited to the video, and a plurality of still images may be displayed in order.

The gaze point detection unit 32 detects position data indicating the position of the gaze point of the subject. In this embodiment, the gaze point detection unit 32 detects the line-of-sight vector of the subject defined in a three-dimensional global coordinate system on the basis of the image data of the right and left eyeballs EB of the subject acquired by the image acquisition device 20. The gaze point detection unit 32 detects the position data of the intersection between the detected line-of-sight vector of the subject and the display unit 11 of the display device 10 as the position data of the gaze point of the subject. That is, in this embodiment, the position data of the gaze point is the position data of the intersection between the line-of-sight vector of the subject defined in the three-dimensional global coordinate system and the display unit 11 of the display device 10. The gaze point detection unit 32 detects the position data of the gaze point of the subject in each defined sampling period. This sampling period can be, for example, a cycle (for example, every 20 (msec)) of the frame synchronization signal output from the imaging device 21.

The region setting unit 33 sets a specific region corresponding to the evaluation video displayed on the display unit 11 of the display device 10. In this embodiment, the region setting unit 33 sets, as the specific region, a moving object region A (see FIG. 5) corresponding to the moving object included in the evaluation video, a movement route region A1 (see FIG. 6) corresponding to the movement route along which the moving object moves according to the movement rule, and a final arrival point region A2 (see FIG. 6) corresponding to the final arrival point of the moving object. In this embodiment, the set region is not displayed on the display unit 11, but is not limited thereto, and may be displayed on the display unit 11.

On the basis of the position data of the gaze point, the determination unit 34 determines whether the gaze point exists in the specific region in the display period in which the task is displayed, in other words, in the display period in which the display operation is performed, and outputs determination data. In this embodiment, on the basis of the position data of the gaze point, the determination unit 34 determines whether the gaze point exists in the moving object region A, the movement route region A1, and a final arrival point region A2 which are the specific regions, and outputs determination data. For example, when determining that the gaze point exists in the specific region, the determination unit 34 adds "1" to a count value which is a determination value of the specific region and outputs determination data. For example, for each determination cycle, the determination unit 34 determines whether the gaze point exists in the specific region. The determination cycle can be, for example, a cycle (for example, every 20 (msec)) of the frame synchronization signal output from the imaging device 21. That is, the determination cycle of determination unit 34 is the same as the sampling period of gaze point detection unit 32.

The calculation unit 35 calculates gaze point data indicating the progress of the movement of the gaze point in the display period on the basis of the determination data which is the determination result of the determination unit 34. In this embodiment, the calculation unit 35 calculates, as the gaze point data, time data indicating an existence time during which the gaze point existed in the specific region in the display period on the basis of the determination data of the determination unit 34. More specifically, the calculation unit 35 calculates, as the time data, first time data in which the gaze point exists in the moving object region A in a time range T4 that the teaching video is displayed, second time data in which the gaze point exists in the movement route region A1 in a time range T7 that the question video is displayed, and third time data in which the gaze point exists in the final arrival point region A2 in the time range T7. Further, the calculation unit 35 includes a counter which counts the number of times of determination that the gaze point exists in the specific region. Further, the calculation unit 35 includes a management timer which manages a playing time of the evaluation video and a detection timer which detects an elapsed time from when the evaluation video is displayed on the display unit 11 of the display device 10.

The evaluation unit 36 obtains evaluation data indicating the evaluation result of the subject on the basis of the time data which is the gaze point data. The evaluation data is data indicating how correctly the subject is visually following the moving object displayed on the display unit 11 of the display device 10 in the display operation, whether the subject can estimate the movement route of the moving object correctly, and whether the subject can estimate the final arrival point correctly.

The input/output control unit 37 acquires data (the image data of the eyeball EB, the input data, and the like) from at least one of the image acquisition device 20 and the input device 50. Further, the input/output control unit 37 outputs the data to at least one of the display device 10 and the output device 40. The input/output control unit 37 may output a task for the subject from the output device 40 such as a speaker.

The storage unit 38 stores therein the position data, the determination data, the time data as the gaze point data, and the evaluation data. Further, the storage unit 38 stores therein an evaluation program for causing a computer to execute a process of displaying the evaluation video, a process of detecting the position of the gaze point of the subject observing the display unit, a process of setting the specific region on the display unit, a process of determining whether the gaze point exists in the specific region on the basis of the position data of the gaze point and outputting the determination data, a process of obtaining the evaluation data of the subject on the basis of the determination data, and a process of outputting the evaluation data.

Evaluation Method

Next, an evaluation method according to this embodiment will be described. In the evaluation method according to this embodiment, the cognitive dysfunction and brain dysfunction of the subject are evaluated by using the above-described evaluation device 100. In this embodiment, contents of a task are to cause the subject to estimate a place where the moving object presented at a predetermined position finally reaches through a predetermined movement route according to the movement rule. For example, the task is to cause the subject to estimate a place where a ball (moving object) MA1 arranged in the upper portion of the evaluation video finally reaches through the predetermined movement route while rolling according to the movement rule.

It is known that symptoms of the cognitive dysfunction and brain dysfunction affect a spatial cognitive ability, an ability to correct an estimation, and a visually following ability. In a case where the subject is not a person with cognitive dysfunction or brain dysfunction, it is possible to accurately recognize the space indicated by the evaluation video and accurately estimate the movement route of the moving object. Further, in a case where the subject is not a person with cognitive dysfunction or brain dysfunction, when a correct movement route is presented, an incorrect estimation can be corrected. Further, in a case where the subject is not a person with cognitive dysfunction or brain dysfunction, it is possible to visually follow the moving object and the presented correct movement route. On the other hand, in a case where the subject is a person with cognitive dysfunction or brain dysfunction, the space indicated by the evaluation video cannot be accurately recognized, and the movement route of the moving object cannot be accurately estimated in some cases. Further, in a case where the subject is a person with cognitive dysfunction or brain dysfunction, an incorrect estimation cannot be corrected even when a correct movement route is presented in some cases. Further, in a case where the subject is a person with cognitive dysfunction or brain dysfunction, the moving object and the presented correct movement route cannot be visually followed in some cases.

For such reasons, for example, the subject can be evaluated by performing the following procedure. First, on the display unit 11 of the display device 10, the ball MA1 before falling and obstacles MB11 to MB16 are illustrated. The obstacles MB11 to MB16 are restraint objects for restraining the movement route along which the ball MA1 moves. The subject is caused to estimate a cup in which the fallen ball MA1 is accommodated. The subject can be evaluated by detecting whether the subject can gaze at the correct movement route and the final arrival point. Further, the subject can be evaluated by detecting whether the subject can gaze at the falling ball MA1 at the time of teaching or answering.

Figure 3:
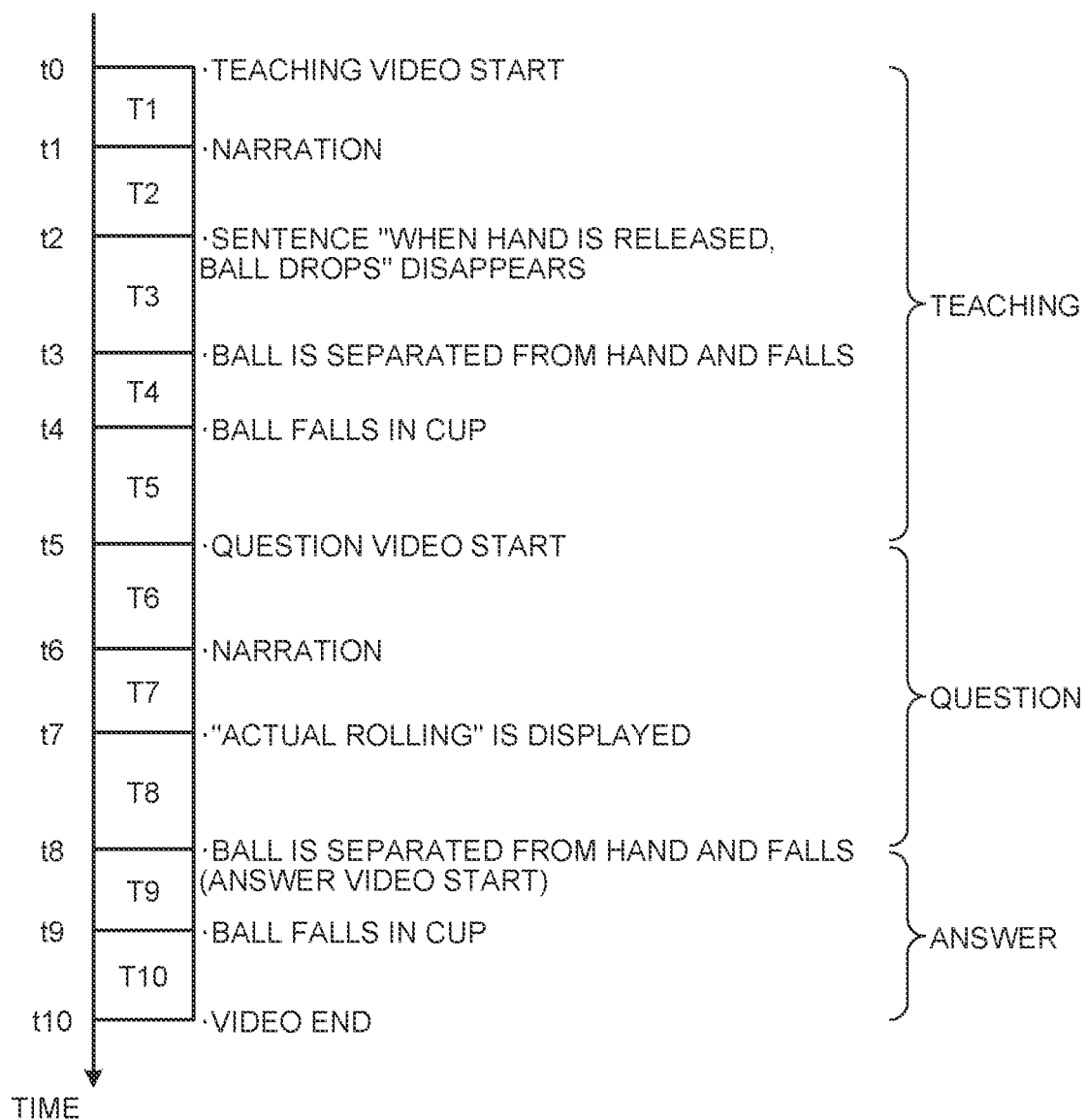
FIG. 3 is a time chart illustrating an example of a timing at which each video of an evaluation video is displayed on a display unit.

FIG. 3 illustrates a time chart of the evaluation video displayed at the time of evaluation of the subject. FIG. 3 is a time chart illustrating an example of a timing at which each video of the evaluation video is displayed on the display unit. The time starts from t0 and shifts to t0, t1, t2, t3, t4, t5, t6, t7, t8, t9, and t10 in this order. Further, a time on or after t0 but before t1 is defined as a time range T1; a time on or after t1 but before t2 is defined as a time range T2; a time on or after t2 but before t3 is defined as a time range T3; a time on or before t3 but before t4 is defined as a time range T4; a time on or after t4 but before t5 is defined as a time range T5; a time on or after t5 but before t6 is defined as a time range T6; a time on or after t6 but before t7 is defined as a time range T7; a time on or after t7 but before t8 is defined as a time range T8; a time on or after t8 but before t9 is defined as a time range T9; and a time on or after t9 but before t10 is defined as a time range T10.

Figure 4:
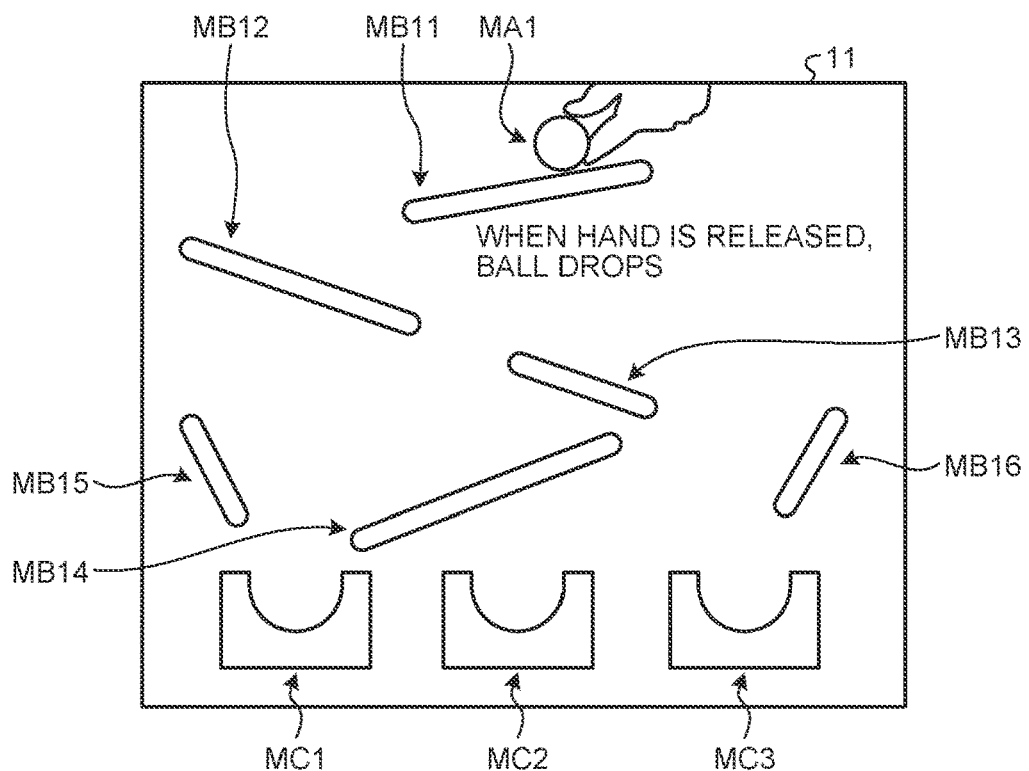
FIG. 4 is a view illustrating an example of the evaluation video displayed on a display unit by a display control unit according to the first embodiment.

First, when the evaluation video is played, the teaching video starts (at t0 in FIG. 3). FIG. 4 is displayed in the time ranges T1 to T3. Next, a narration "when the hand is released, the ball drops" is given (at t1 in FIG. 3). Next, a sentence "when the hand is released, the ball drops" displayed in FIG. 4 disappears (at t2 in FIG. 3). As the narration, characters may be display, or voice may be output.

FIG. 4 is a view illustrating an example of the evaluation video displayed on the display device 10 by the display control unit 31. The display control unit 31 causes the display unit 11 of the display device 10 to display the teaching video for the task of causing the subject to gaze at the movement route of the movement according to the movement rule and the final arrival point. In this embodiment, the display control unit 31 causes the display unit 11 of the display device 10 to display the ball MA1, which is a moving object, before falling, the obstacles MB11 to MB16 which are restraint objects for restraining the movement route along which the ball MA1 moves, and three cups MC1 to MC3 which are fall destination candidates.

The ball MA1 is displayed on the upper portion of the display unit 11 of the display device 10. When the ball MA1 is separated from the hand, the ball MA1 falls due to gravity, and moves according to the movement rule in which the movement route is restrained by the obstacles MB11 to MB16.

The obstacles MB11 to MB16 are plate-like obstacles displayed below the ball MA1. The obstacles MB11 to MB16 are obstacles guiding the falling route of the ball MA1. The shapes of the obstacles MB11 to MB16 are not limited thereto, and may be other articles. The obstacles MB11 to MB16 are arranged to be inclined with respect to a vertical direction. The ball MA1 falls while rolling on the obstacles MB11 to MB16. The obstacles MB11 to MB16 are arranged apart from each other. The obstacles MB11 to MB16 guide the ball MA1 to the cup MC1 which is the final arrival point while restricting the fall of the ball MA1.

The cup MC1 is displayed in the lower left portion of the display unit 11 of the display device 10. The cup MC1 has a cup shape opened upward. The cup MC1 is displayed at a position where the ball MA1 separated from the hand falls and reaches while rolling on the obstacle MB11, the obstacle MB12, and the obstacle MB14.

The cup MC2 and the cup MC3 are displayed at the lower center and the lower right portions of the display unit 11 of the display device 10. The cup MC2 and the cup MC3 have a cup shape opened upward. The cup MC2 and the cup MC3 have the same shape and size as the cup MC1. The cup MC2 and the cup MC3 are comparison arrival points, and are displayed at positions different from the position at which the ball MA1 separated from the hand falls and reaches while rolling on the obstacle MB11, the obstacle MB12, and the obstacle MB14.

The display control unit 31 may display an explanatory sentence of the teaching in order to cause the subject to estimate the movement route of the ball MA1 in the time range T1. The explanatory sentence is displayed, for example, in a region along the upper side of the display unit 11 of the display device 10. For example, "when the hand is released, the ball drops" is displayed as the explanatory sentence. Instead of the explanatory sentence, the description may be given by voice.

Figure 5:
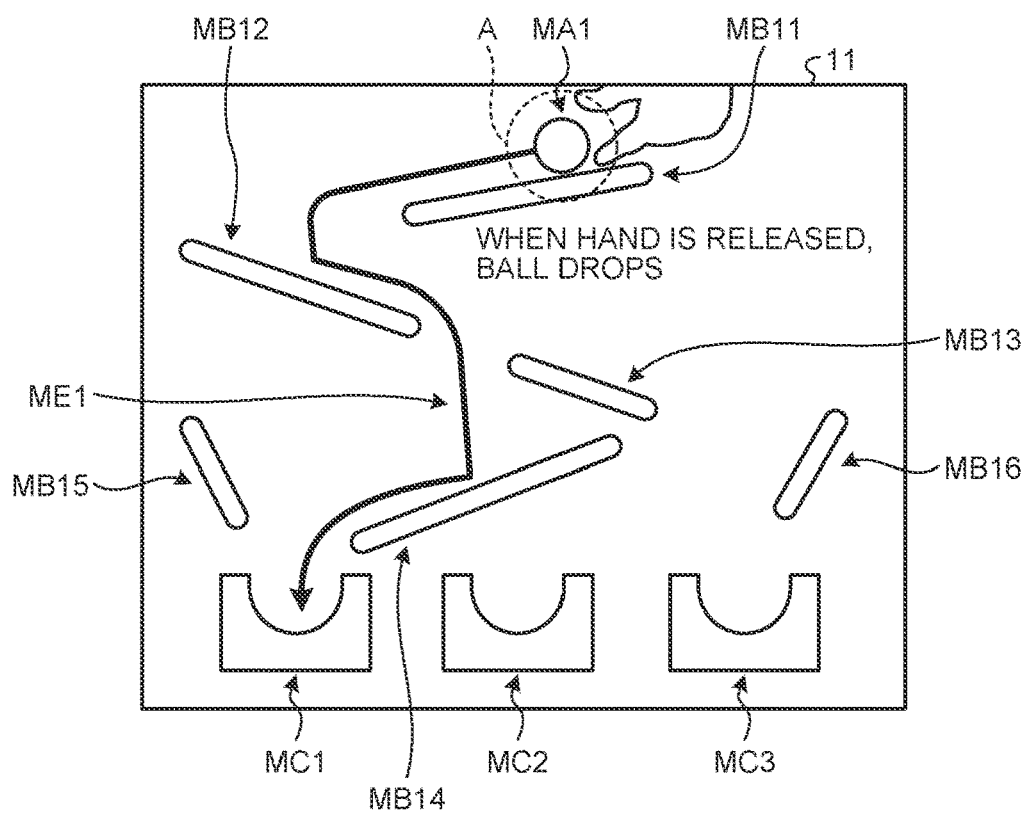
FIG. 5 is a view illustrating the example of the evaluation video displayed on the display unit by the display control unit according to the first embodiment.

After the time ranges T1 to T3 elapse, the teaching video illustrated in FIG. 5 is displayed in the time ranges T4 and T5. First, the ball MA1 is separated from the hand and rolls down (at t3 in FIG. 3). The ball MA1 which has rolled down finally falls in the cup MC1 (at t4 in FIG. 3), and the teaching video ends (at t5 in FIG. 3).

FIG. 5 is a view illustrating an example of the evaluation video displayed on the display device 10 by the display control unit 31. FIG. 5 is displayed after FIG. 4. The display control unit 31 causes the display unit 11 of the display device 10 to display a video in which the finger supporting the ball MA1 is released so that the ball MA1 falls through between the obstacles MB11 to MB16. The display control unit 31 causes the display unit 11 of the display device 10 to display a video in which the fallen ball MA1 falls in the left cup MC1 among the three cups MC1 to MC3 at the lower portion of the screen.

In the time range T4, the region setting unit 33 sets, as the specific region, the moving object region A corresponding to the ball MA1 although the region is not displayed on the display unit 11 of the display device 10. The moving object region A is set to a range including the ball MA1, for example. The center position of the moving ball MA1 is known in advance. The region setting unit 33 sets a predetermined size of region set around the ball MA1 as the moving object region A which moves in accordance with the movement of the center position of the ball MA1.

The subject gazes at the movement of the ball MA1 in the teaching video. In the case of the subject having cognitive dysfunction such as dementia or brain dysfunction, it is difficult to visually follow the ball MA1 falling while rolling due to degradation in the visually following ability. When the gaze point is gathered in the moving object region A, the subject can understand that there is little problem in the eye followability.

Figure 6:
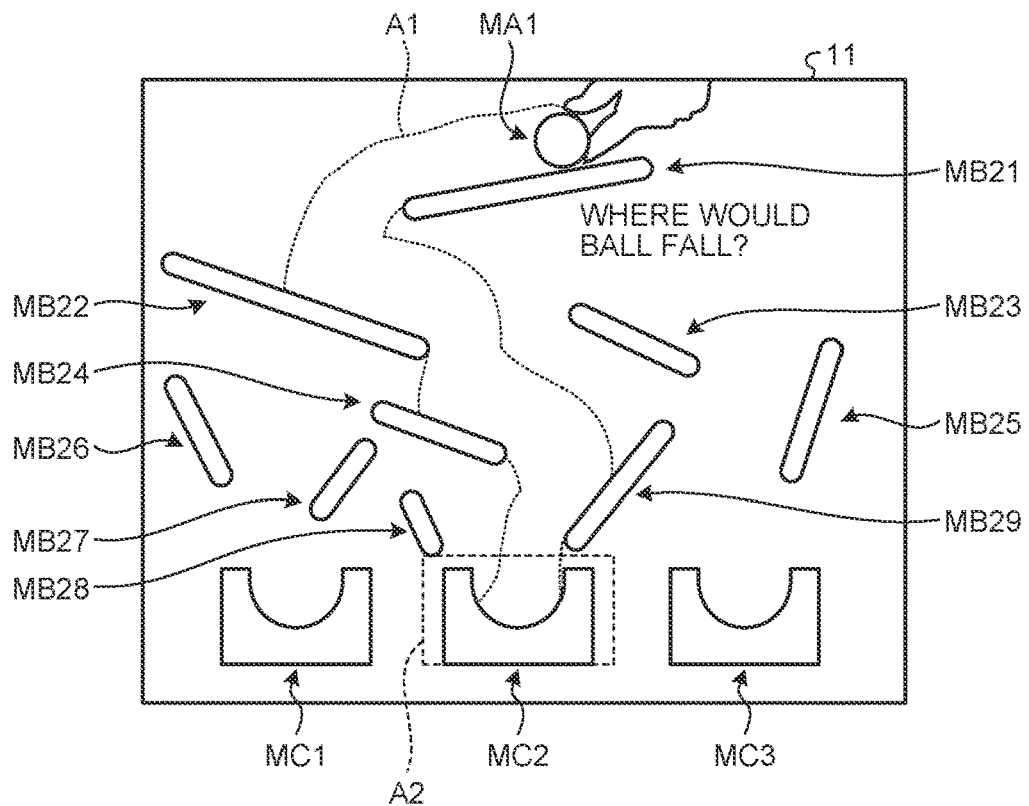
FIG. 6 is a view illustrating the example of the evaluation video displayed on the display unit by the display control unit according to the first embodiment.

After the end of the teaching video, the question video starts (at t5 in FIG. 3). In the time ranges T6 to T8, the question video illustrated in FIG. 6 is displayed. Next, a narration "where would the ball fall?" is given (t6 in FIG. 3). Next, the sentence "where would the ball fall?" is replaced with "actual rolling" (at t7 in FIG. 3). The question video ends (at t8 in FIG. 3). As the narration, characters may be display, or voice may be output.

FIG. 6 is a view illustrating an example of the evaluation video displayed on the display device 10 by the display control unit 31. The display control unit 31 causes the display unit 11 of the display device 10 to display the question video for the task of causing the subject to gaze at the movement route of the movement according to the movement rule and the final arrival point. The display control unit 31 causes the display unit 11 of the display device 10 to display the ball MA1 before falling, the obstacles MB21 to MB29 arranged differently from the teaching video, and the explanatory sentence. For example, "where would the ball fall?" is displayed as the explanatory sentence. Instead of the explanatory sentence, the description may be given by voice.

In the time range T7, the region setting unit 33 sets, as the specific regions, the movement route region A1 corresponding to the movement route of the ball MA1 and the final arrival point region A2 corresponding to the cup MC2 which is the final arrival point although the regions A1 and A2 are not displayed on the display unit 11 of the display device 10. The region setting unit 33 sets the movement route region A1 on the basis of, for example, the trajectory of the moving ball MA1. The movement route region A1 is set to correspond to the trajectory of the ball MA1 in the state of extending along the obstacle MB21, the obstacle MB22, the obstacle MB24, and the obstacle MB29 from the upper portion to the lower portion of the drawing in the display unit 11 of the display device 10. A region having a predetermined size set around the cup MC2 is set as the final arrival point region A2.

In the question video, the subject observes which route the ball MA1 passes through and which cup among the three cups MC1 to MC3 the ball MA1 finally falls in. In the case of the subject having cognitive dysfunction such as dementia or brain dysfunction, it is difficult to accurately estimate which route the ball MA1 can pass through due to degradation in a spatial cognitive function or the like. When the gaze points are gathered in the movement route region A1 and the final arrival point region A2, it can be seen that the subject can correctly estimate the movement route of the ball MA1, and there are few problems in the spatial cognitive ability.

By measuring the line-of-sight at the time of displaying the question video, it is possible to record a thought process of the subject, such as whether the route along which the ball MA1 falls can be quickly estimated at one time or whether the estimation is repeated from the start position many times, and to assist diagnosis.

Figure 7:
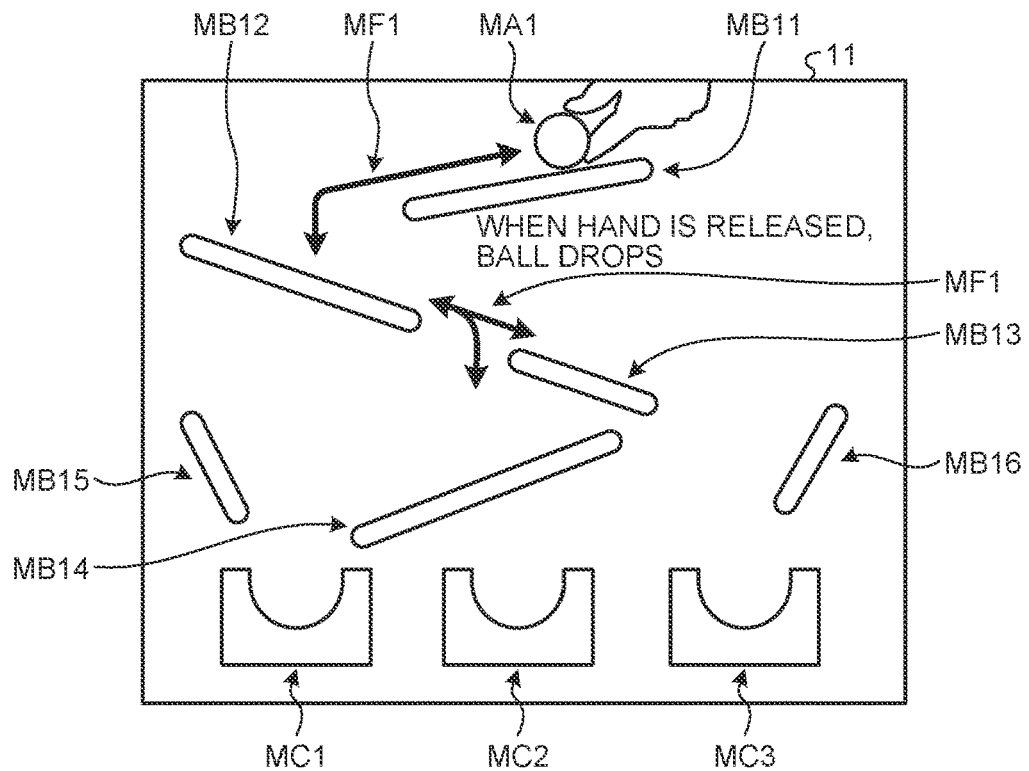
FIG. 7 is a view illustrating the evaluation video displayed on the display unit by the display control unit according to the first embodiment and a record of an example of a thought process of a subject.

Here, the thought process of the subject will be described with reference to FIG. 7. FIG. 7 is a view illustrating the evaluation video displayed on the display unit by the display control unit according to the first embodiment and a record of an example of the thought process of the subject. A thick arrow indicates a route MF1 of the gaze point of the subject. It can be understood from the route MF1 that the subject has failed in estimation up to the final arrival point region A2 and has repeatedly performed estimation at a branch point or the like on the way to the final arrival point region A2. In this way, when the route MF1 is used as an assist for diagnosis, it is possible to diagnose the subject more appropriately.

Figure 8:
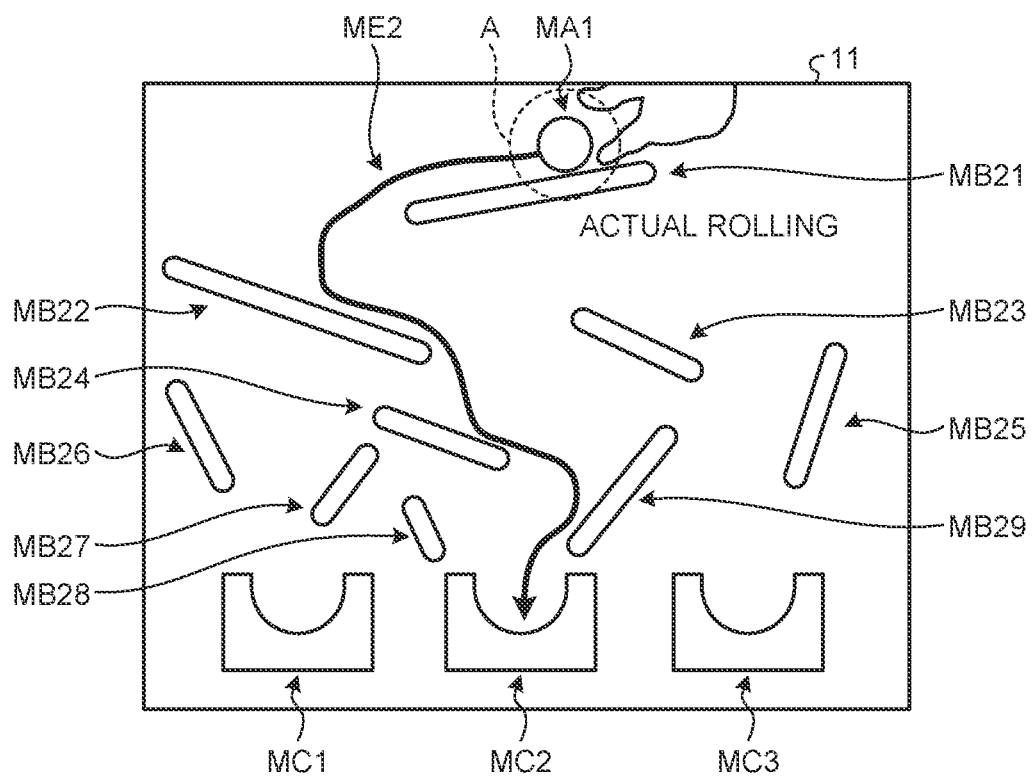
FIG. 8 is a view illustrating the example of the evaluation video displayed on the display unit by the display control unit according to the first embodiment.

After the question video ends, the answer video starts. In the time ranges T9 and T10, the answer video illustrated in FIG. 8 is displayed. First, the ball MA1 is separated from the hand and rolls down (at t8 in FIG. 3). Next, the ball MA1 falls in the cup MC2 (at t9 in FIG. 3), the answer video ends, and the evaluation video ends (t10 in FIG. 3).

FIG. 8 is a view illustrating an example of the evaluation video displayed on the display device 10 by the display control unit 31. FIG. 8 is displayed after FIG. 6. The display control unit 31 causes the display unit 11 of the display device 10 to display the answer video of the task. The display control unit 31 causes the display unit 11 of the display device 10 to display, for example, "actual rolling" as an explanatory sentence. Instead of the explanatory sentence, the description may be given by voice. For example, the display control unit 31 causes the display unit 11 of the display device 10 to display a movement route ME2 in which the ball MA1 is separated from the hand, falls while rolling along the obstacle MB21, the obstacle MB22, the obstacle MB24, and the obstacle MB29, and is accommodated in the cup MC2.

By displaying the answer video, it is possible to intuitively notify the subject of the movement route ME2 of the ball MA1. The answer video may not be displayed. In this way, after the time range T10 elapses, the playing of the evaluation video ends. In the time range T10, the end of the evaluation video may be displayed on the display unit 11 of the display device 10.

In the time range T4, the determination unit 34 determines whether the gaze point exists in the moving object region A, and outputs determination data. Further, in the time range T4, the calculation unit 35 calculates the first time data (moving object region existence time data) indicating the existence time during which the gaze point exists in the moving object region A on the basis of the determination data.

In the time range T7, the determination unit 34 determines whether the gaze point exists in each of the movement route region A1 and the final arrival point region A2, and outputs determination data. Further, in the time range T7, the calculation unit 35 calculates the second time data (final arrival point region existence time data) indicating the time during which the gaze point exists in the final arrival point region A2 and third time data (movement route region existence time data) indicating the time during which the gaze point exists in the movement route region A1 on the basis of the determination data.

In this embodiment, it can be estimated that the existence time during which the gaze point exists in the moving object region A, the movement route region A1, or the final arrival point region A2 is longer, as the number of times that the determination unit 34 determines that the gaze point exists therein is larger. Therefore, in this embodiment, the time data can be the number of times that the determination unit 34 determines that the gaze point exists in the moving object region A, the movement route region A1, or the final arrival point region A2 within the display period, for example. That is, the time data can be the number of the gaze points detected in the moving object region A, the movement route region A1, or the final arrival point region A2 within the display period. The calculation unit 35 can calculate the time data by using a count result of a counter provided in the determination unit 34.

In this embodiment, in a case where the evaluation unit 36 obtains the evaluation data on the basis of the time data, for example, the following can be performed.

First, the counter provided in the calculation unit 35 counts the first time data in the time range T4, and counts the second time data and the third time data in the time range T7. Here, the count result of the counter in the first time data is set to a counter value CNT1, the count result of the counter in the second time data is set to a counter value CNT2, and the count result of the counter in the third time data is set to a counter value CNT3.

In this case, the evaluation unit 36 can obtain an evaluation value ANS for obtaining the evaluation data as follows. For example, in the time range T4, the evaluation value ANS can be obtained by determining the length of time during which the gaze point of the subject exists in the moving object region A. In a case where the subject keeps gazing at the ball MA1 with following visually, the time to gaze at the moving object region A lengthens. In the time range T4, as the existence time of the gaze point existing in the moving object region A is longer, the value of the counter value CNT1 becomes larger. Alternatively, for example, the evaluation value ANS can be obtained by determining the length of time during which the gaze point of the subject exists in the movement route region A1 or the final arrival point region A2 in the time range T7. In a case where the subject correctly estimates the movement route of the ball MA1 and keeps gazing at the ball MA1, the time to gaze at the movement route region A1 or the final arrival point region A2 lengthens. In the time range T7, as the existence time of the gaze point existing in the movement route region A1 or the final arrival point region A2 is longer, the values of the counter value CNT2 and the counter value CNT3 becomes larger. Accordingly, the evaluation value ANS can be obtained by determining whether the total value of the counter values CNT1, CNT2, and CNT3 is a predetermined value or more. For example, in a case where the total value of the counter values CNT1, CNT2, and CNT3 is equal to or more than a predetermined value, it can be evaluated that the possibility that the subject is a person with cognitive dysfunction or brain dysfunction is low. Further, in a case where the total value of the counter values CNT1, CNT2, and CNT3 is less than a predetermined value, it can be evaluated that the possibility that the subject is a person with cognitive dysfunction or brain dysfunction is high.

The predetermined value can be, for example, the average value of the total values of the counter values CNT1, CNT2, and CNT3 of the subjects who are not persons with cognitive dysfunction or brain dysfunction, or a value set on the basis of that average value. Alternatively, the predetermined value may be, for example, the lowest value of the total value of the counter values CNT1, CNT2, and CNT3 of the subjects who are not persons with cognitive dysfunction or brain dysfunction. In such cases, the predetermined value may be set in advance for each age and gender, and a value corresponding to the age and gender of the subject may be used.

The evaluation unit 36 can obtain the evaluation value ANS by, for example, following formula (1). The counter value CNT1 indicates an evaluation as to whether the subject can visually follow the ball MA1 at the time of teaching. The counter value CNT2 is a value corresponding to a correct answer, and thus the evaluation of this count value is the most important. The counter value CNT3 is a value leading the correct answer, and thus the evaluation of this count value is important.

$$ANS = (K1 \times CNT1) + (K2 \times CNT2) + (K3 \times CNT3) \qquad (1)$$

In the above formula (1), constants K1, K2, and K3 are weighting constants. The constants K1, K2, and K3 can satisfy, for example, the relation of K1<K3<K2. In this case, the evaluation value ANS is obtained in which the influence of the third time data is weighted more than the influence of the first time data, and the influence of the second time data is weighted more than the influence of the third time data.

Alternatively, the constants K1, K2, and K3 may be set to an equal value (for example, 1), and the evaluation value ANS may be obtained without weighting. In this way, when the evaluation data is obtained on the basis of the first time data, the second time data, and the third time data, it is possible to subdivide and evaluate the visually following ability in the time ranges T4 and T5, the ability to correct the estimation, and the spatial cognitive ability in the time ranges T6 to T8.

The evaluation unit 36 determines whether the evaluation value ANS is equal to or greater than a predetermined threshold value, and determines the evaluation. For example, in a case where the evaluation value ANS is equal to or more than a threshold value, it is possible to determine the evaluation that the possibility that the subject has cognitive dysfunction or brain dysfunction is low. Further, in a case where the evaluation value ANS is not equal to or more than the predetermined threshold value, it is possible to determine the evaluation that the possibility that the subject has cognitive dysfunction or brain dysfunction is high.

In this embodiment, in a case where the evaluation unit 36 outputs an evaluation result, the input/output control unit 37 causes the output device 40 to output, for example, character data of "the subject is considered to be unlikely to be a person with cognitive dysfunction or brain dysfunction", character data of "the subject is considered to be likely to be a person with cognitive dysfunction or brain dysfunction", or the like according to the evaluation result.

Figure 9:
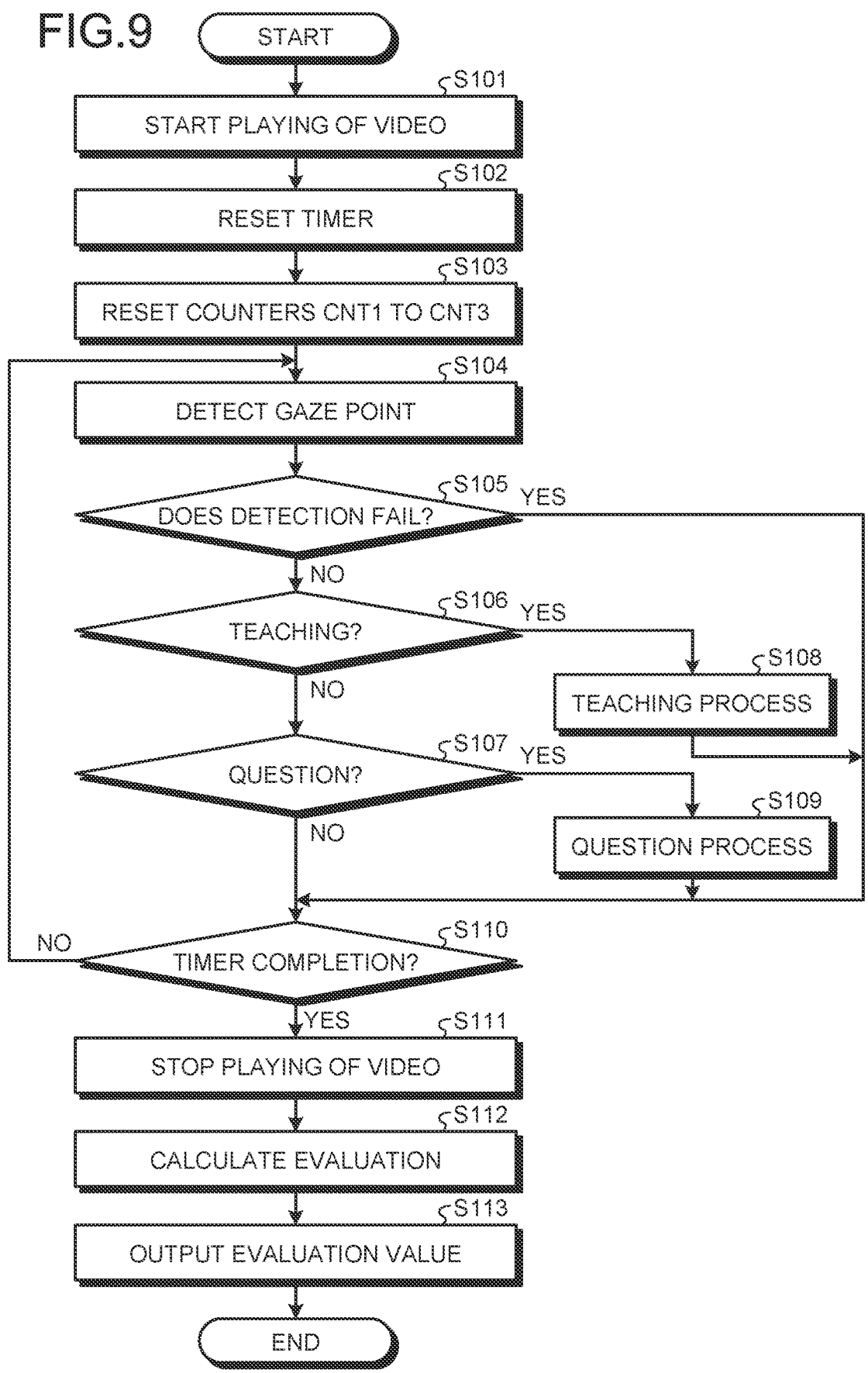
FIG. 9 is a flowchart illustrating an example of an evaluation method according to the first embodiment.

Next, an example of the evaluation method according to this embodiment will be described with reference to FIG. 9. FIG. 9 is a flowchart illustrating an example of the evaluation method according to the first embodiment.

The display control unit 31 starts the playing of the evaluation video (step S101). The evaluation video illustrated in FIGS. 4, 5, 6, and 8 is sequentially displayed on the display unit 11 of the display device 10. Then, the process proceeds to step S102.

The calculation unit 35 resets the timer which manages the playing time of the evaluation video (step S102). More specifically, the calculation unit 35 resets the management timer which manages the playing time of the evaluation video and the detection timer which detects the period to which the currently played evaluation video belongs in the time range T1 to the time range T10 in the time chart illustrated in FIG. 3, and starts measurement of each timer. Then, the process proceeds to step S103.

The determination unit 34 resets each of the counter values CNT1, CNT2, and CNT3 for measuring the time when the gaze point exists in the specific region to zero and starts measurement (step S103). In this embodiment, the gaze point measurement is performed once for each frame of the camera, and thus the gaze time can be measured by counting correspondingly to the region being gazed for each frame. Then, the process proceeds to step S104.

In a state where the evaluation video displayed on the display unit 11 of the display device 10 is shown to the subject, the gaze point detection unit 32 detects the position data of the gaze point of the subject on the display unit 11 of the display device 10 every specified sampling period (for example, 20 (msec)) (step S104). Then, the process proceeds to step S105.

With considering a case where the gaze point cannot be detected due to blinking or the like, the calculation unit 35 determines whether the detection of the gaze point fails (step S105). In a case where the calculation unit 35 determines that the detection of the gaze point fails (Yes in step S105), the process proceeds to step S110. In a case where the calculation unit 35 determines that the detection of the gaze point does not fail (No in step S105), the process proceeds to step S106.

In a case where it is determined that the detection of the gaze point does not fail (No in step S105), the calculation unit 35 determines whether it is a period for displaying the teaching video (step S106). More specifically, the calculation unit 35 determines whether the detection result of the detection timer indicates the time ranges T1 to T5. In a case where the calculation unit 35 determines that the detection result of the detection timer corresponds to the range of the time ranges T1 to T5, and it is the period for displaying the teaching video (Yes in step S106), the process proceeds to step S108. In a case where the calculation unit 35 determines that the detection result of the detection timer does not corresponds to the range of the time ranges T1 to T5, and it is not the period for displaying the teaching video (No in step S106), the process proceeds to step S107.

In a case where it is determined that it is not the period for displaying the teaching video (No in step S106), the calculation unit 35 determines whether it is the period for displaying the question video (step S107). More specifically, the calculation unit 35 determines whether the detection result of the detection timer indicates the time ranges T6 to T8. In a case where the calculation unit 35 determines that the detection result of the detection timer corresponds to the range of the time ranges T6 to T8, and it is the period for displaying the question video (Yes in step S107), the process proceeds to step S109. In a case where the calculation unit 35 determines that the detection result of the detection timer does not corresponds to the range of the time ranges T6 to T8, and it is not the period for displaying the question video (No in step S107), the process proceeds to step S110.

The calculation unit 35 executes teaching process to be described later (step S108). Then, the process proceeds to step S110.

The calculation unit 35 executes question process to be described later (step S109). Then, the process proceeds to step S110.

The calculation unit 35 determines whether the playing of the evaluation video reaches a completion time on the basis of the detection result of the management timer (step S110). In a case where the calculation unit 35 determines that the playing of the evaluation video does not reach the completion time (No in step S110), the process in step S104 and subsequent processes are repeated. In a case where the calculation unit 35 determines that the playing of the evaluation video reaches the completion time (Yes in step S110), the process proceeds to step S111.

The display control unit 31 stops the playing of the evaluation video (step S111). Then, the process proceeds to step S112.

The evaluation unit 36 calculates the evaluation value ANS on the basis of the time data obtained from the above processing result (step S112). Then, the process proceeds to step S113.

The input/output control unit 37 outputs the evaluation data obtained by the evaluation unit 36 (step S113). The process is ended.

Figure 10:
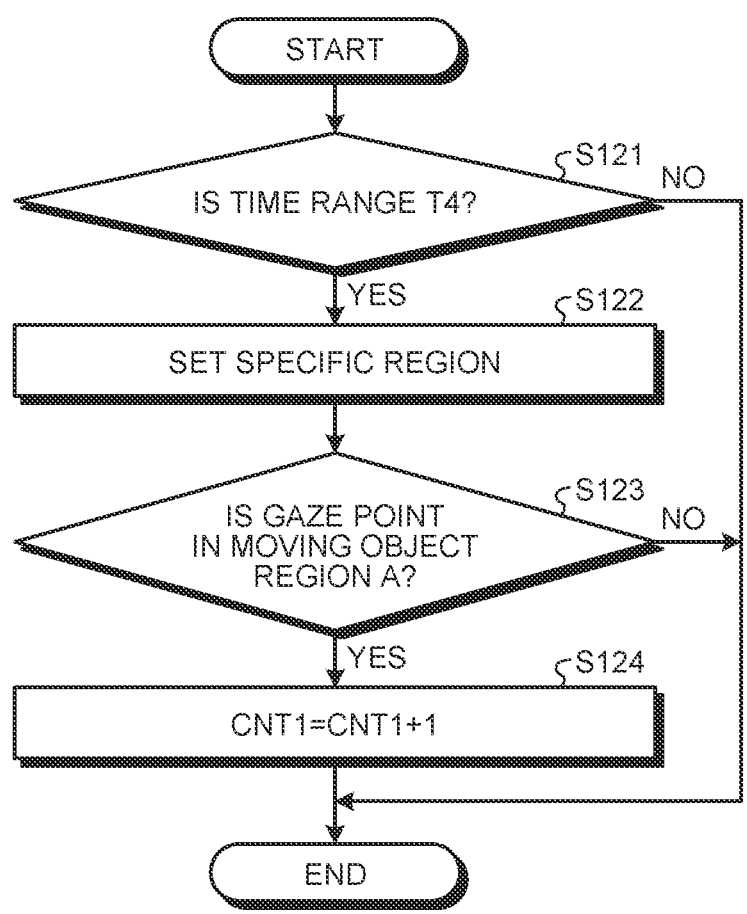
FIG. 10 is a flowchart illustrating an example of teaching process.

Next, an example of the teaching process will be described with reference to FIG. 10. FIG. 10 is a flowchart illustrating an example of the teaching process.

The calculation unit 35 determines whether the detection result of the detection timer indicates the time range T4 (step S121). In a case where the calculation unit 35 determines that the detection result of the detection timer corresponds to the time range T4 (Yes in step S121), the process proceeds to step S122. In a case where the calculation unit 35 determines that the detection result of the detection timer does not correspond to the time range T4 (No in step S121), the process is ended.

In a case where the calculation unit 35 determines that the detection result of the detection timer corresponds to the time range T4 (Yes in step S121), the region setting unit 33 sets the moving object region A as the specific region in order to check whether the subject gazes at the region to be viewed (step S122). Then, the process proceeds to step S123.

The determination unit 34 determines whether the gaze point of the subject exists in the moving object region A (step S123). In a case where the determination unit 34 determines that the gaze point of the subject exists in the moving object region A (Yes in step S123), the process proceeds to step S124. In a case where the determination unit 34 determines that the gaze point of the subject does not exist in the moving object region A (No in step S123), the process is ended.

In a case where the determination unit 34 determines that the gaze point exists in the moving object region A (Yes in step S123), the calculation unit 35 increments the counter value CNT1 by one (step S124). The calculation unit 35 outputs the counter value CNT1 as determination data.

Figure 11:
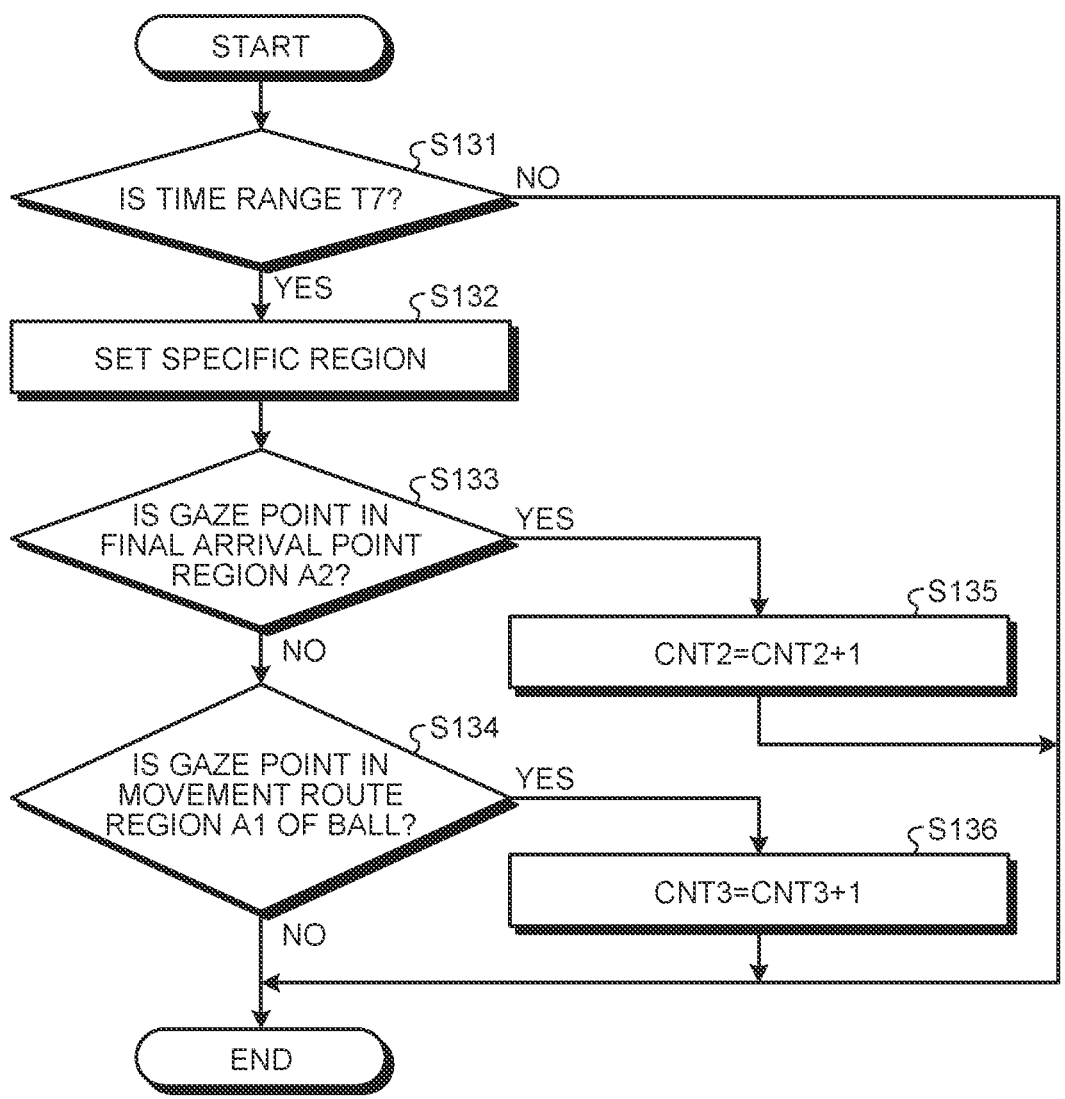
FIG. 11 is a flowchart illustrating an example of question process.

Next, an example of the question process will be described with reference to FIG. 11. FIG. 11 is a flowchart illustrating an example of the question process.

The calculation unit 35 determines whether the detection result of the detection timer indicates the time range T7 (step S131). In a case where the calculation unit 35 determines that the detection result of the detection timer corresponds to the time range T7 (Yes in step S131), the process proceeds to step S132. In a case where the calculation unit 35 determines that the detection result of the detection timer does not correspond to the time range T7 (No in step S131), the process is ended.

In a case where the calculation unit 35 determines that the detection result of the detection timer corresponds to the time range T7 (Yes in step S131), the region setting unit 33 sets the movement route region A1 and the final arrival point region A2 as the specific regions in order to check whether the subject gazes at the region to be viewed (step S132). Then, the process proceeds to step S133.

The determination unit 34 determines whether the gaze point of the subject exists in the final arrival point region A2 (step S133). In a case where the determination unit 34 determines that the gaze point of the subject exists in the final arrival point region A2 (Yes in step S133), the process proceeds to step S135. In a case where the determination unit 34 determines that the gaze point of the subject does not exist in the final arrival point region A2 (No in step S133), the process proceeds to step S134.

In a case where the determination unit 34 determines that the gaze point of the subject does not exist in the final arrival point region A2 (No in step S133), it is determined whether the gaze point of the subject exists in the movement route region A1 (step S134). In a case where the determination unit 34 determines that the gaze point of the subject exists in the movement route region A1 (Yes in step S134), the process proceeds to step S136. In a case where the determination unit 34 determines that the gaze point of the subject does not exist in the movement route region A1 (No in step S134), the process is ended.

In a case where the determination unit 34 determines that the gaze point exists in the final arrival point region A2 (Yes in step S133), the calculation unit 35 increments the counter value CNT2 by one (step S135). The calculation unit 35 outputs the counter value CNT2 as determination data.

In a case where the determination unit 34 determines that the gaze point exists in the movement route region A1 (Yes in step S134), the calculation unit 35 increments the counter value CNT3 by one (step S136). The calculation unit 35 outputs the counter value CNT3 as determination data.

As described above, the evaluation device 100 according to this embodiment includes: the display unit 11 that displays an image; the gaze point detection unit 32 that detects position data of a gaze point of a subject; the display control unit 31 that performs a display operation of displaying, on the display unit 11, a task of causing the subject to gaze at a movement route of a movement according to a movement rule and a final arrival point; the region setting unit 33 that sets the movement route region A1 corresponding to the movement route and the final arrival point region A2 corresponding to the final arrival point; the determination unit 34 that determines, on the basis of the position data of the gaze point, whether the gaze point exists in the movement route region A1 and the final arrival point region A2 in a display period in which the display operation is performed; the calculation unit 35 that calculates gaze point data indicating the progress of movement of the gaze point in the display period on the basis of the determination result of the determination unit 34; and the evaluation unit 36 that obtains evaluation data of the subject on the basis of the gaze point data.

The evaluation method according to this embodiment includes: displaying an image on the display unit 11; detecting position data of a gaze point of a subject observing the display unit 11; performing a display operation of displaying, on the display unit 11, a task of causing the subject to gaze at a movement route of a movement according to a movement rule and a final arrival point; setting the movement route region A1 corresponding to the movement route and the final arrival point region A2 corresponding to the final arrival point; determining, on the basis of the position data of the gaze point, whether the gaze point exists in the movement route region A1 and the final arrival point region A2 in a display period in which the display operation is performed; calculating gaze point data indicating the progress of movement of the gaze point in the display period on the basis of the determination result of the determining; and obtaining evaluation data of the subject on the basis of the gaze point data.

The evaluation program according to this embodiment causes a computer to execute: displaying an image on the display unit 11; detecting position data of a gaze point of a subject observing the display unit 11; performing a display operation of displaying, on the display unit 11, a task of causing the subject to gaze at a movement route of a movement according to a movement rule and a final arrival point; setting the movement route region A1 corresponding to the movement route and the final arrival point region A2 corresponding to the final arrival point; determining, on the basis of the position data of the gaze point, whether the gaze point exists in the movement route region A1 and the final arrival point region A2 in a display period in which the display operation is performed; calculating gaze point data indicating the progress of movement of the gaze point in the display period on the basis of the determination result of the determining; and obtaining evaluation data of the subject on the basis of the gaze point data.

According to this embodiment, the time data indicating that the gaze point of the subject exists in the specific region in the display period is obtained, and the evaluation data of the subject is obtained on the basis of the time data. Therefore, the evaluation device 100 can evaluate the spatial cognitive ability, the ability to correct the estimation, and the visually following ability for the subject on the basis of the movement of the line-of-sight of the subject in the display period. Accordingly, the evaluation device 100 can evaluate the subject with high accuracy.

In this embodiment, the calculation unit 35 calculates the first time data in which the gaze point exists in the moving object region A in the time ranges T4 to T5, the second time data in which the gaze point exists in the movement route region A1 in the time range T7, and the third time data in which the gaze point exists in the final arrival point region A2 in the time range T7, and the evaluation unit 36 obtains the evaluation data on the basis of the first time data, the second time data, and the third time data. Accordingly, in this embodiment, it is possible to subdivide and evaluate the visually following ability in the time ranges T4 and T5, the ability to correct the estimation, and the spatial cognitive ability in the time ranges T6 to T8.

In the evaluation device 100 according to this embodiment, the evaluation unit 36 obtains the evaluation data by weighting the influence of the third time data rather than the influence of the first time data and further weighting the influence of the second time data rather than the influence of the third time data. The evaluation value ANS is obtained by weighting the second time data and the third time data, whereby the evaluation data can be efficiently obtained.

In the evaluation device 100 according to this embodiment, the region setting unit 33 sets the moving object region A as the specific region on the basis of the trajectory of the ball MA1 in the time range T4 that the teaching video is displayed. Accordingly, the moving object region A can be accurately set according to the movement of the ball MA1, thereby obtaining the time data with high accuracy.

In the evaluation device 100 according to this embodiment, the region setting unit 33 sets, as the specific region, the movement route region A1 corresponding to the movement route of the ball MA1 and the final arrival point region A2 corresponding to the cup MC2 as the final arrival point in the time range T7 that the question video is displayed. Accordingly, the movement route region A1 and the final arrival point region A2 can be set with high accuracy, thereby obtaining the time data with high accuracy.

In the evaluation device 100 according to this embodiment, the display control unit 31 causes the correct movement route of the ball MA1 to be displayed on the teaching video. Accordingly, it is possible to notify the subject of how the ball MA1 falls. When the subject is notified of how the ball MA1 falls, the subject has an opportunity to correct his/her estimation in a case where the estimation is wrong. Accordingly, the ability to correct the estimation can be included in the evaluation.

Second Embodiment

Figure 12:
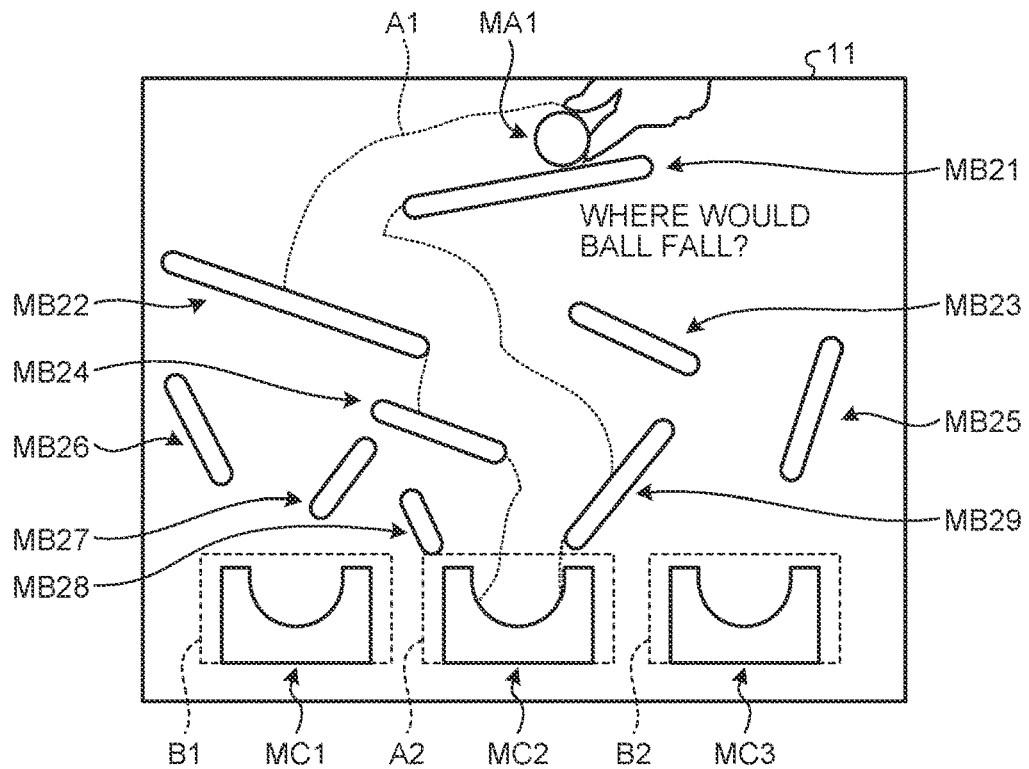
FIG. 12 is a view illustrating an example of an evaluation video displayed on a display unit by a display control unit according to a second embodiment.
Figure 13:
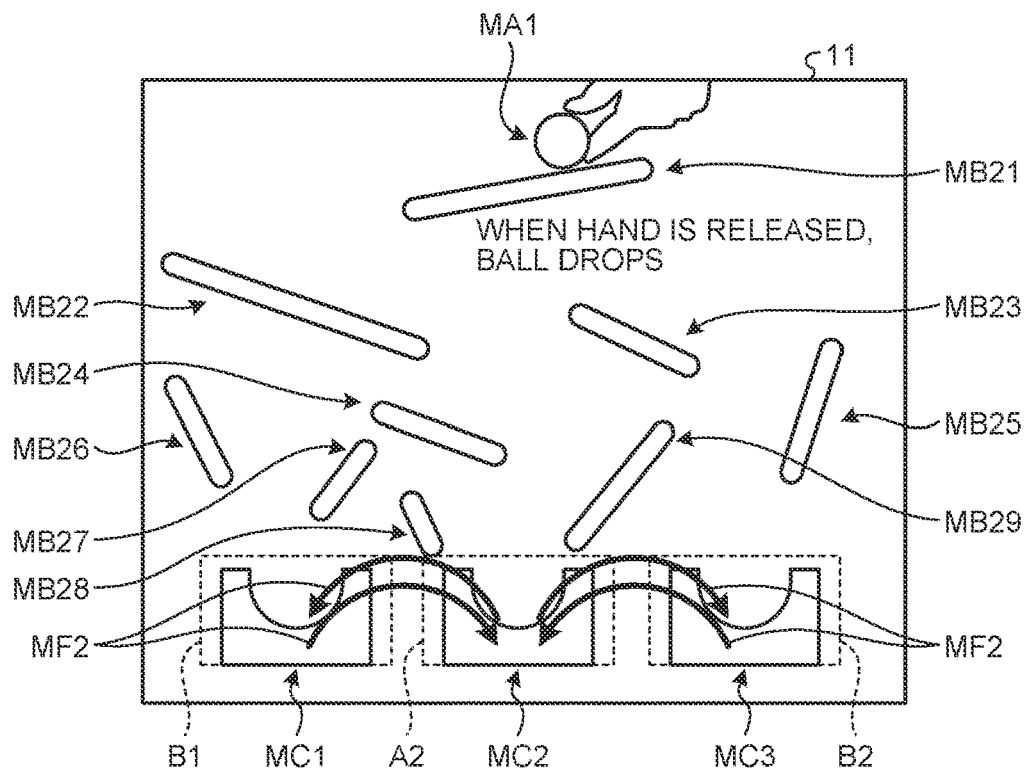
FIG. 13 is a view illustrating the evaluation video displayed on the display unit by the display control unit according to the second embodiment and an example of the thought process of the subject.
Figure 14:
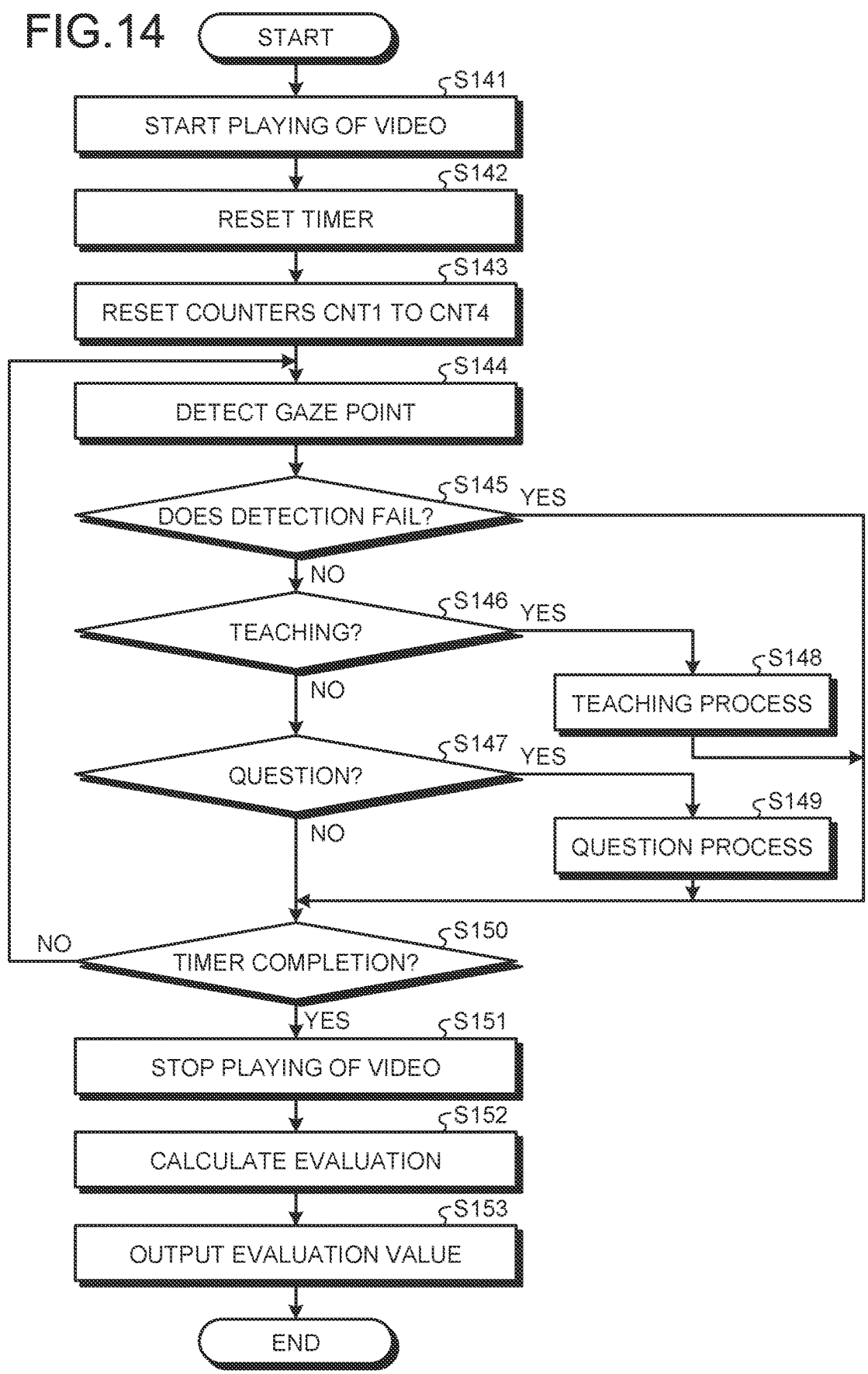
FIG. 14 is a flowchart illustrating an example of an evaluation method according to the second embodiment.
Figure 15:
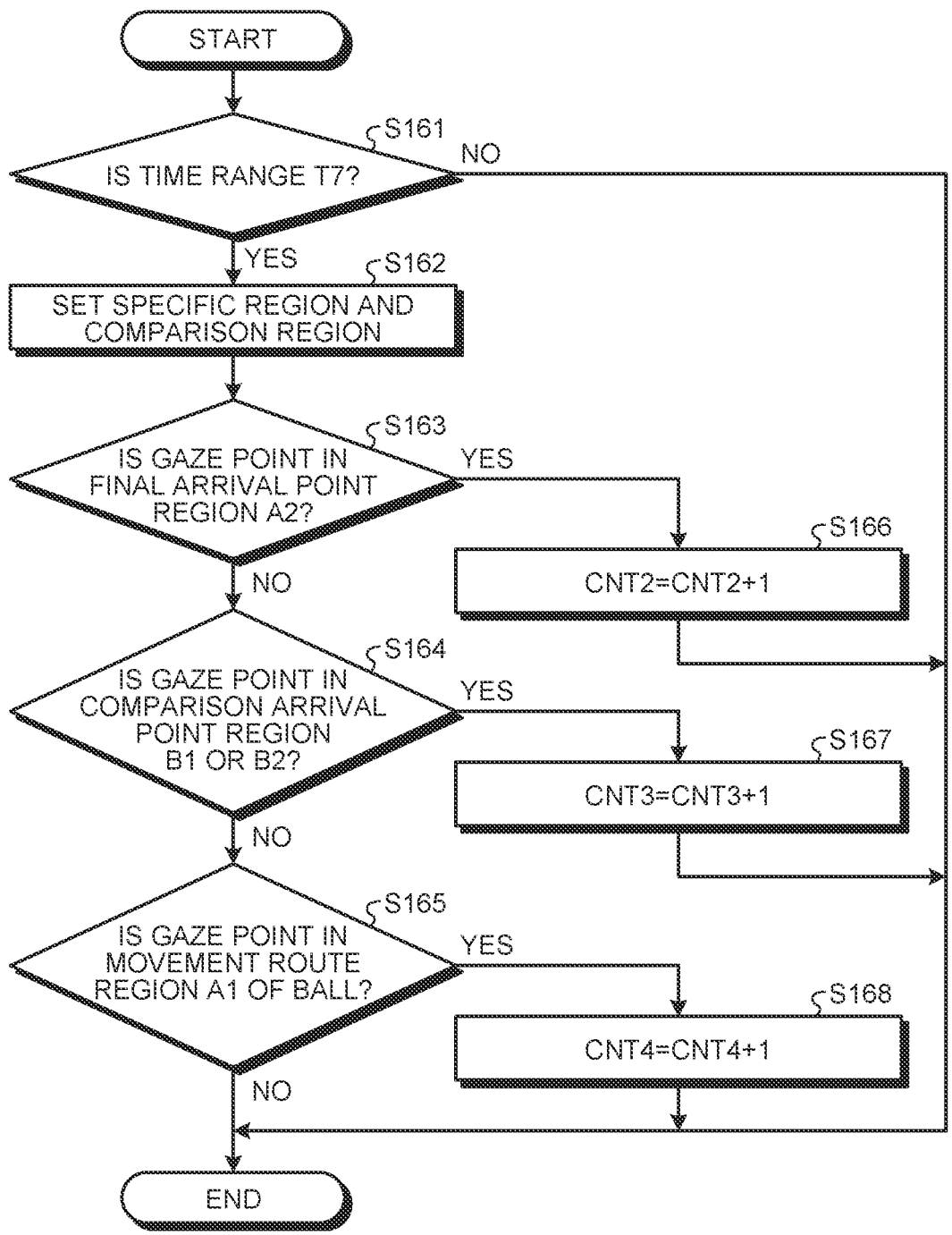
FIG. 15 is a flowchart illustrating an example of the question process.

The evaluation device 100 according to this embodiment will be described with reference to FIGS. 12 to 15. FIG. 12 is a view illustrating an example of an evaluation video displayed on the display device 10 by the display control unit 31 according to a second embodiment. FIG. 13 is a view illustrating the evaluation video displayed on the display unit by the display control unit according to the second embodiment and an example of the thought process of the subject. FIG. 14 is a flowchart illustrating an example of an evaluation method according to the second embodiment. FIG. 15 is a flowchart illustrating an example of the question process. The basic configuration of the evaluation device 100 is similar to that of the evaluation device 100 of the first embodiment. In the following description, the same components as those of the evaluation device 100 of the first embodiment are denoted by the same reference numerals or corresponding reference numerals, and a detailed description thereof will be omitted. This embodiment is different from the first embodiment in processing performed in the region setting unit 33, the determination unit 34, and the evaluation unit 36.

The region setting unit 33 sets a specific region and a comparison region corresponding to the evaluation video displayed on the display unit 11 of the display device 10. In the time range T7, the region setting unit 33 sets the comparison region in at least a part of the region other than the specific region included in the evaluation video. In this embodiment, in the time range T7, in addition to the movement route region A1 and the final arrival point region A2, the region setting unit 33 sets comparison arrival point regions B1 and B2 corresponding to the comparison arrival points as the comparison regions.

On the basis of the position data of the gaze point, the determination unit 34 determines whether the gaze point exists in the movement route region A1 and determines whether the gaze point exists in at least the final arrival point region A2 among the final arrival point region A2 and the comparison arrival point regions B1 and B2.

FIG. 12 is a view illustrating an example of the evaluation video displayed on the display device 10 by the display control unit 31. In the time range T7 during which FIG. 12 is displayed, the region setting unit 33 sets, as the specific regions, the movement route region A1 and the final arrival point region A2 although the regions are not displayed on the display unit 11 of the display device 10. The region setting unit 33 sets the comparison arrival point regions B1 and B2 as the comparison regions although the regions are not displayed on the display unit 11 of the display device 10. A region having a predetermined size set around the cup MC1 is set as the comparison arrival point region B1. A region having a predetermined size set around the cup MC3 is set as the comparison arrival point region B2.

When the gaze points are gathered in the comparison arrival point region B1 and the comparison arrival point region B2, it can be seen that the subject cannot correctly estimate the movement route of the ball MA1, and there is a problem in the spatial cognitive ability. Further, when the line-of-sight with respect to the comparison arrival point region B1 and the comparison arrival point region B2 is measured, it is possible to record the thought process of the subject, such as whether the route along which the ball MA1 falls can be quickly estimated at one time or whether the estimation is repeated many times, and to assist diagnosis.

Here, the thought process of the subject will be described with reference to FIG. 13. Thick arrows indicate routes MF2 of the gaze point of the subject. It can be seen from the routes MF2 that the subject cannot estimate where the final arrival point region A2 is and is confused between the final arrival point region A2, the comparison arrival point region B1, and the comparison arrival point region B2, so that the line-of-sight goes back and forth. In this way, by using the routes MF2 as the assist of diagnosis, it is possible to diagnose the subject more appropriately.

In the time range T7, the determination unit 34 performs a determination on whether the gaze point exists in the movement route region A1 and at least the final arrival point region A2 among the final arrival point region A2 and the comparison arrival point regions B1 and B2, and outputs determination data. Further, in the time range T7, the calculation unit 35 calculates, on the basis of the determination data, the second time data (final arrival point region existence time data) indicating the time during which the gaze point exists in the final arrival point region A2, third time data (comparison arrival point region existence time data) indicating the time during which the gaze point exists in the comparison arrival point regions B1 or B2, and fourth time data (movement route region existence time data) indicating the time during which the gaze point exists in the movement route region A1.

The evaluation unit 36 can obtain the evaluation value ANS by, for example, following formula (2). The counter value CNT1 indicates an evaluation as to whether the subject can visually follow the ball MA1 at the time of teaching. The counter value CNT2 is a value corresponding to a correct answer, and thus the evaluation of this count value is the most important. Since the counter value CNT3 is a value corresponding to an incorrect answer, the evaluation of this count value is low. Since the counter value CNT4 is a value leading the correct answer, and thus the evaluation of this count value is important.

$$ANS=(K1 \times CNT1)+(K2 \times CNT2)+(K3 \times CNT3)+(K4 \times CNT4) \quad (2)$$

In above formula (2), the constants K1, K2, K3, and K4 are weighting constants. The constants K1, K2, K3, and K4 can satisfy, for example, the relation of K1<K3<K4<K2. In this case, an evaluation value ANS is obtained in which the influence of the third time data is weighted more than the influence of the first time data, the influence of the fourth time data is weighted more than the influence of the third time data, and the influence of the second time data is weighted more than the influence of the fourth time data.

Next, an example of the evaluation method according to this embodiment will be described with reference to FIG. 14. The processing of step S141, step S142, and steps S144 to S153 is similar to the processing of step S101, step S102, and steps S104 to S113 of the flowchart illustrated in FIG. 9.

The determination unit 34 resets each of the counter values CNT1, CNT2, CNT3, and CNT4 for measuring the time when the gaze point exists in the specific region to zero and starts measurement (step S143). Then, the process proceeds to step S144.

Next, an example of the question process will be described with reference to FIG. 15. The processing of step S161, step S163, step S165, and step S166 is similar to the processing of step S131, step S133, step S134, and step S135 in FIG. 11.

In a case where the calculation unit 35 determines that the detection result of the detection timer corresponds to the time range T7 (Yes in step S161), the region setting unit 33 sets the movement route region A1 and the final arrival point region A2 as the specific regions and sets the comparison arrival point regions B1 and B2 as the comparison regions in order to check whether the subject gazes at the region to be viewed (step S162). Then, the process proceeds to step S163.

In a case where the determination unit 34 determines that the gaze point of the subject does not exist in the final arrival point region A2 (No in step S163), it is determined whether the gaze point of the subject exists in the comparison arrival point regions B1 or B2 (step S164). In a case where the determination unit 34 determines that the gaze point of the subject exists in the comparison arrival point regions B1 or B2 (Yes in step S164), the process proceeds to step S167. In a case where the determination unit 34 determines that the gaze point of the subject does not exist in the comparison arrival point regions B1 or B2 (No in step S164), the process proceeds to step S165.

In a case where the determination unit 34 determines that the gaze point exists in the comparison arrival point regions B1 or B2 (Yes in step S164), the calculation unit 35 increments the counter value CNT3 by one (step S167). The calculation unit 35 outputs the counter value CNT3 as determination data.

In a case where the determination unit 34 determines that the gaze point exists in the movement route region A1 (Yes in step S165), the calculation unit 35 increments the counter value CNT4 by one (step S168). The calculation unit 35 outputs the counter value CNT4 as determination data.

As described above, in this embodiment, the time data indicating that the gaze point of the subject exists in the specific region and the comparison region in the display period is obtained, and the evaluation data of the subject is obtained on the basis of the time data. In this embodiment, it can be determined and evaluated that the subject gazes at the comparison arrival point regions B1 and B2 corresponding to the cups MC1 and MC3 that are not the final arrival point. According to this embodiment, the evaluation of the subject can be performed with high accuracy.

Third Embodiment

Figure 16:
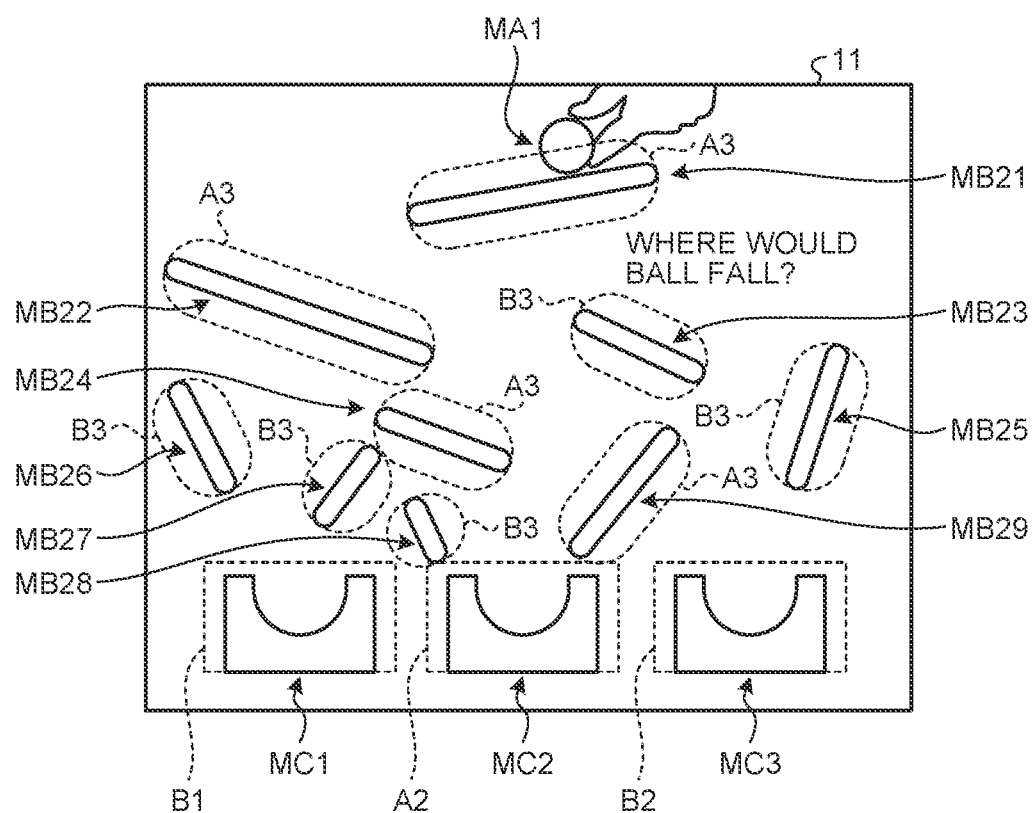
FIG. 16 is a view illustrating an example of an evaluation video displayed on a display unit by a display control unit according to a third embodiment.
Figure 17:
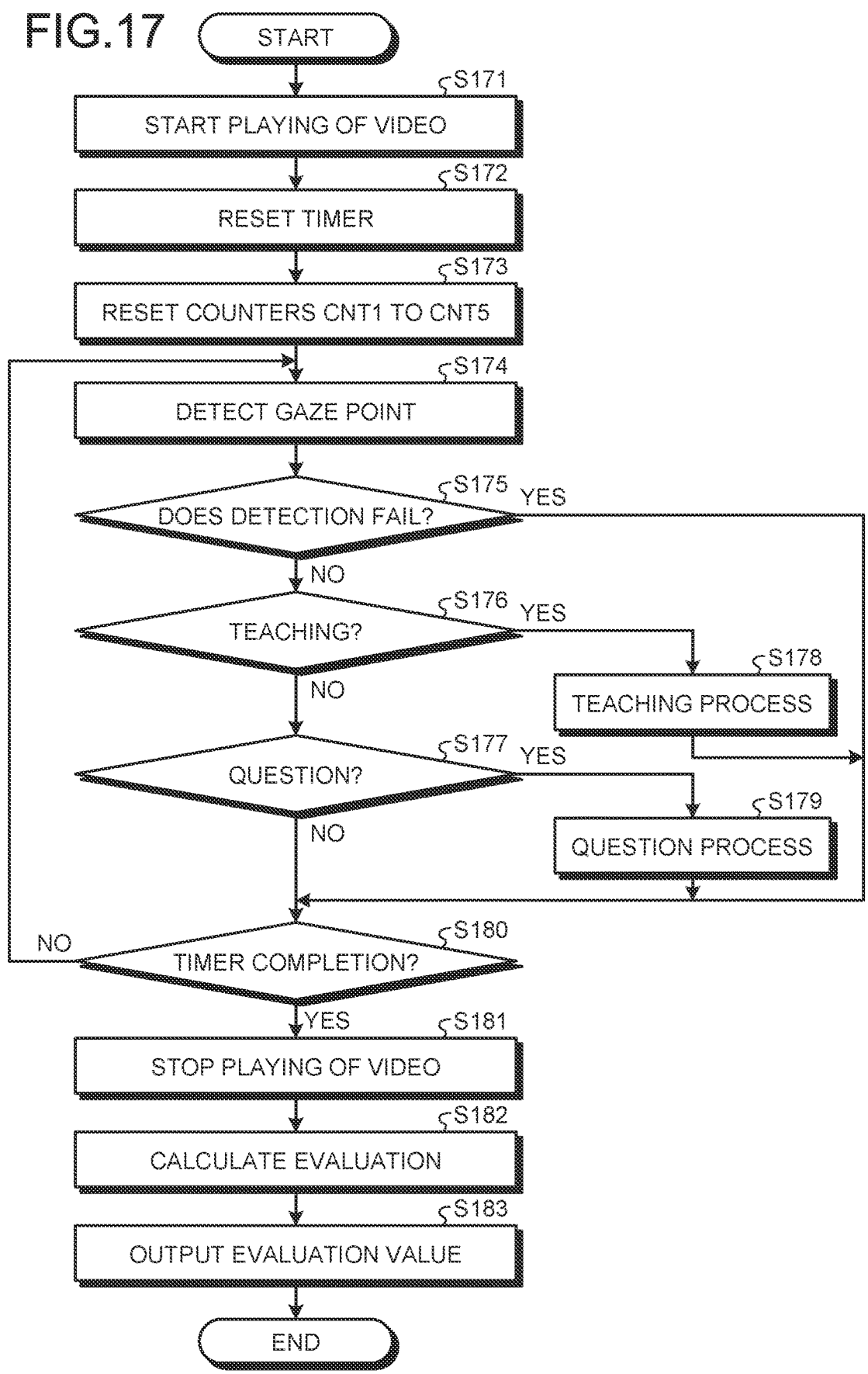
FIG. 17 is a flowchart illustrating an example of an evaluation method according to the third embodiment.
Figure 18:
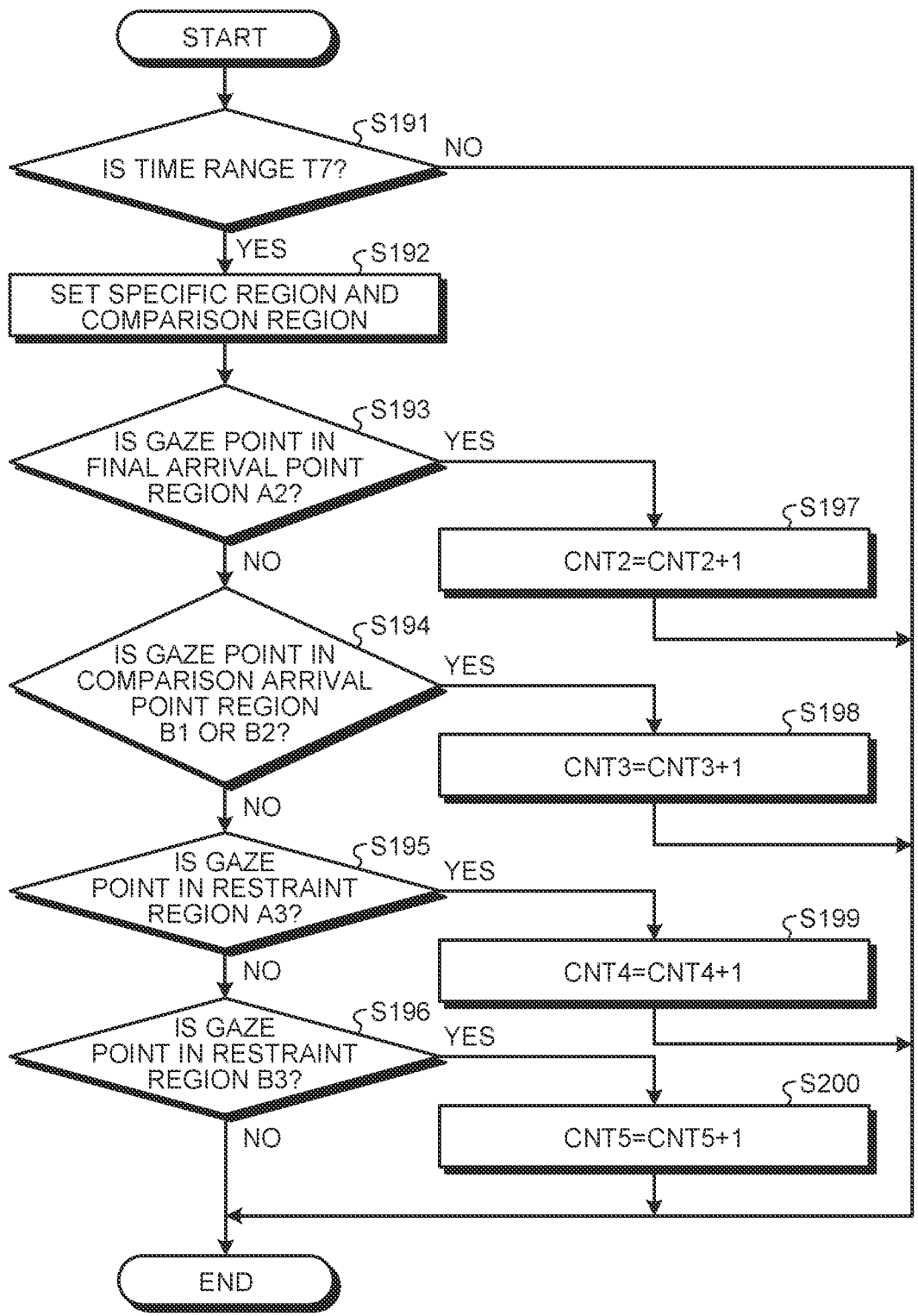
FIG. 18 is a flowchart illustrating an example of the question process.

The evaluation device 100 according to this embodiment will be described with reference to FIGS. 16 to 18. FIG. 16 is a view illustrating an example of an evaluation video displayed on the display device 10 by the display control unit 31 according to a third embodiment. FIG. 17 is a flowchart illustrating an example of an evaluation method according to the third embodiment. FIG. 18 is a flowchart illustrating an example of the question process. This embodiment is different from the first embodiment in processing of the region setting unit 33 and the evaluation unit 36.

The region setting unit 33 sets a specific region and a comparison region corresponding to the evaluation video displayed on the display unit 11 of the display device 10. In this embodiment, in the time range T7, in addition to the final arrival point region A2, the region setting unit 33 sets, as the specific region, a restraint object region A3 corresponding to the restraint object positioned on the movement route of the moving object among the restraint objects. In the time range T7, the region setting unit 33 sets, as the comparison region, a restraint object region B3 corresponding to the restraint object positioned out of the movement route of the moving object among the restraint objects. The region setting unit 33 sets the comparison arrival point regions B1 and B2 corresponding to the comparison arrival points as the comparison regions.

On the basis of the position data of the gaze point, the determination unit 34 determines whether the gaze point exists in the restraint object region A3 or the restraint object region B3 and at least the final arrival point region A2 among the final arrival point region A2 and the comparison arrival point regions B1 and B2.

FIG. 16 is a view illustrating an example of an evaluation video displayed on the display device 10 by the display control unit 31. In the time range T7 that FIG. 16 is displayed, the region setting unit 33 sets, as the specific regions, the final arrival point region A2 and the restraint object region A3 although the regions are not displayed on the display unit 11 of the display device 10. The region setting unit 33 sets the comparison arrival point regions B1 and B2 and the restraint object region B3 as the comparison regions although the regions are not displayed on the display unit 11 of the display device 10. A predetermined size of region set around the restraint object which comes into contact when the ball MA1 falls is set as the restraint object region A3. A predetermined size of region set around the restraint object which does not come into contact when the ball MA1 falls is set as the restraint object region B3.

When the gaze points are gathered in the final arrival point region A2 and the restraint object region A3, it can be understood that the subject can correctly estimate the movement route of the ball MA1, and there are few problems in the spatial cognitive ability. When the gaze points are gathered in the comparison arrival point regions B1 and B2 and the restraint object region B3, it can be seen that the subject cannot correctly estimate the movement route of the ball MA1, and there is a problem in the spatial cognitive ability. Further, when the line-of-sight with respect to the restraint object region A3 and the restraint object region B3 is measured, it is possible to record the thought process of the subject, such as whether the route along which the ball MA1 falls can be estimated appropriately or whether the route can be estimated accidentally, and to assist diagnosis.

In the time range T7, the determination unit 34 performs each determination on whether the gaze point exists in the restraint object region A3 or the restraint object region B3 and at least the final arrival point region A2 among the final arrival point region A2 and the comparison arrival point regions B1 and B2, and outputs determination data. Further, in time range T7, the calculation unit 35 calculates, on the basis of the determination data, the second time data (final arrival point region existence time data) indicating the time during which the gaze point exists in the final arrival point region A2, the third time data (comparison arrival point region existence time data) indicating the time during which the gaze point exists in the comparison arrival point regions B1 and B2, fourth time data (restraint object region existence time data) indicating the time during which the gaze point exists in the restraint object region A3, and fifth time data (restraint object region existence time data) indicating the time during which the gaze point exists in the restraint object region B3.

The evaluation unit 36 can calculate the evaluation value ANS by, for example, following formula (3). The counter value CNT1 means an evaluation of whether the subject can visually follow the ball MA1 at the time of teaching. The counter value CNT2 means a portion of a correct answer, and thus the evaluation of this count value is the most important. Since the counter value CNT3 is an incorrect answer, the evaluation of this count value is low. Since the counter value CNT4 is a portion leading the correct answer, and thus the evaluation of this count value is important. Since the counter value CNT5 is an incorrect answer, the evaluation of this count value is low.

$$ANS=(K1 \times CNT1)+(K2 \times CNT2)+(K3 \times CNT3)+(K4 \times CNT4)+(K5 \times CNT5) \quad (3)$$

In above formula (3), the constants K1, K2, K3, K4, and K5 are constants for weighting. The constants K1, K2, K3, K4, and K5 can satisfy, for example, K1<K5<K3<K4<K2. In this case, an evaluation value ANS is calculated in which the influence of the fifth time data is weighted more than the influence of the first time data, the influence of the third time data is weighted more than the influence of the fifth time data, the influence of the fourth time data is weighted more than the influence of the third time data, and the influence of the second time data is weighted more than the influence of the fourth time data.

Next, an example of the evaluation method according to this embodiment will be described with reference to FIG. 17. The processing of step S171, step S172, and steps S174 to S183 is similar to the processing of step S101, step S102, and steps S104 to S113 of the flowchart illustrated in FIG. 9.

The determination unit 34 resets each of the counter values CNT1, CNT2, CNT3, CNT4, and CNT5 for measuring the time when the gaze point exists in the specific region to zero and starts measurement (step S173). Then, the process proceeds to step S174.

Next, an example of the question process will be described with reference to FIG. 18. The processing in steps S191 to step S194, S197, and S198 is similar to the processing in steps S161 to S164, S166, and S167 in FIG. 15.

In a case where the determination unit 34 determines that the gaze point of the subject does not exist in the comparison arrival point regions B1 and B2 (No in step S194), it is determined whether the gaze point of the subject exists in the restraint object region A3 (step S195). In a case where the determination unit 34 determines that the gaze point of the subject exists in the restraint object region A3 (Yes in step S195), the process proceeds to step S199.

In a case where determination unit 34 determines that the gaze point of the subject does not exist in restraint object region A3 (No in step S195), it is determined whether the gaze point of the subject exists in the restraint object region B3 (step S196). In a case where the determination unit 34 determines that the gaze point of the subject exists in the restraint object region B3 (Yes in step S196), the process proceeds to step S200. In a case where the determination unit 34 determines that the gaze point of the subject does not exist in the restraint object region B3 (No in step S196), the process is ended.

In a case where the determination unit 34 determines that the gaze point exists in the restraint object region A3 (Yes in step S195), the calculation unit 35 increments the counter value CNT4 by one (step S199). The calculation unit 35 outputs the counter value CNT4 as determination data.

In a case where the determination unit 34 determines that the gaze point exists in the restraint object region B3 (Yes in step S196), the calculation unit 35 increments the counter value CNT5 by one (step S200). The calculation unit 35 outputs the counter value CNT5 as determination data.

As described above, in this embodiment, the time data in which the gaze point of the subject exists in the specific region and the comparison region in the display period is obtained, and the evaluation data of the subject is obtained on the basis of the time data. In this embodiment, it can be determined and evaluated that the subject gazes at the restraint object region B3 corresponding to the restraint object with which the ball MA1 does not come into contact when falling. According to this embodiment, the evaluation of the subject can be performed with high accuracy.

The technical scope of the present disclosure is not limited to the above embodiments, and can be appropriately modified without departing from the gist of the present invention.

In the above embodiments, an example has been described in which the evaluation unit 36 adds values obtained by multiplying the counter values CNT1, CNT2, CNT3, and the like by respective constants in the case of obtaining the evaluation value ANS, but the present invention is not limited thereto. For example, the evaluation unit

36 may obtain the evaluation value ANS by individually determining each value of the counter values CNT1, CNT2, CNT3, and the like.

In the above embodiment, a case where the evaluation device 100 is used as an evaluation device for evaluating the possibility of being a person with cognitive dysfunction or brain dysfunction has been described as an example, but the present invention is not limited thereto. For example, the evaluation device 100 may be used as an evaluation device which evaluates the spatial cognitive ability, the ability to correct the estimation, and the visually following ability for the subject who is not a person with cognitive dysfunction or brain dysfunction such as developmental disability.

In the third embodiment, the existence of the gaze point may be determined in a state where the restraint object region B3 is distinguished into the restraint object region corresponding to the restraint object adjacent to the restraint object region A3 and the restraint object region corresponding to the restraint object away from the restraint object region A3. Accordingly, the evaluation of the subject can be performed with higher accuracy.

For example, in the time ranges T9 and T10 that the answer video is displayed, the determination unit 34 may determine whether the gaze point exists in the moving object region A and output the determination data. Accordingly, the evaluation of the subject can be performed with higher accuracy.

As described above, the present disclosure can improve the certainty of the selection of the final result by using the progress without determining only the final result, and as a result, can improve the accuracy of the evaluation. Further, the present disclosure can be used for a question, such as a maze or a ladder lot, in which a progress is displayed.

According to the present disclosure, it is possible to provide the evaluation device, the evaluation method, and the evaluation program capable of evaluating a subject with high accuracy.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An evaluation device comprising:
    a display unit;
    a gaze point detection unit that detects a position of a gaze point of a subject observing the display unit;
    a display control unit that causes the display unit to display a video for a task of causing the subject to gaze at a final arrival point of a moving object;
    a region setting unit that sets a movement route region corresponding to a movement route along which the moving object moves according to a movement rule and a final arrival point region corresponding to the final arrival point;
    a determination unit that determines, based on the position of the gaze point, whether the gaze point exists in the movement route region and the final arrival point region before the moving object starts moving in a display period in which the video for the task is displayed;
    a calculation unit that calculates gaze point data in the display period based on a determination result of the determination unit; and
    an evaluation unit that obtains evaluation data of the subject based on the gaze point data.

2. The evaluation device according to claim 1, wherein
    the video for the task includes a restraint object which restrains the movement route and a comparison arrival point different from the final arrival point,
    the region setting unit further sets a restraint object region corresponding to the restraint object and a comparison arrival point region corresponding to the comparison arrival point, and
    the determination unit performs a determination on the gaze point by using at least one of the movement route region or the restraint object region and using at least the final arrival point region among the final arrival point region and the comparison arrival point region.

3. The evaluation device according to claim 2, wherein
    the gaze point data includes
        at least one type of data of movement route region existence time data indicating an existence time during which the gaze point exists in the movement route region in the display period and restraint object region existence time data indicating an existence time during which the gaze point exists in the restraint object region in the display period, and
        at least final arrival point region existence time data among the final arrival point region existence time data indicating an existence time during which the gaze point exists in the final arrival point region in the display period and comparison arrival point region existence time data indicating an existence time during which the gaze point exists in the comparison arrival point region in the display period, and
    the evaluation unit obtains the evaluation data by weighting at least one type of data included in the gaze point data.

4. An evaluation method comprising:
    displaying an image on a display unit;
    detecting a position of a gaze point of a subject observing the display unit;
    causing the display unit to display a video for a task of causing the subject to gaze at a final arrival point of a moving object;
    setting a movement route region corresponding to a movement route along which the moving object moves according to a movement rule and a final arrival point region corresponding to the final arrival point;
    determining, based on the position of the gaze point, whether the gaze point exists in the movement route region and the final arrival point region before the moving object starts moving in a display period in which the video for the task is displayed;
    calculating gaze point data in the display period based on a determination result of the determining; and
    obtaining evaluation data of the subject based on the gaze point data.

5. A non-transitory computer-readable recording medium containing an evaluation program causing a computer to execute:
    displaying an image on a display unit;
    detecting a position of a gaze point of a subject observing the display unit;
    causing the display unit to display a video for a task of causing the subject to gaze at a final arrival point of a moving object;
    setting a movement route region corresponding to a movement route along which the moving object moves according to a movement rule and a final arrival point region corresponding to the final arrival point;

determining, based on the position of the gaze point, whether the gaze point exists in the movement route region and the final arrival point region before the moving object starts moving in a display period in which the video for the task is displayed;

calculating gaze point data in the display period based on a determination result of the determining; and obtaining evaluation data of the subject based on the gaze point data.

* * * * *